(12) United States Patent
Fukuhara et al.

(10) Patent No.: US 12,156,574 B2
(45) Date of Patent: Dec. 3, 2024

(54) MOLDING APPARATUS

(71) Applicant: YKK Corporation, Tokyo (JP)

(72) Inventors: Yoshiyuki Fukuhara, Toyama (JP); Hiroyuki Yamashita, Toyama (JP); Takahiro Fuse, Toyama (JP); Isamu Michihata, Toyama (JP); Yui Hashimoto, Toyama (JP)

(73) Assignee: YKK Corporation, Tokyo (JP)

( * ) Notice: Subject to any disclaimer, the term of this patent is extended or adjusted under 35 U.S.C. 154(b) by 759 days.

(21) Appl. No.: 17/129,115

(22) Filed: Dec. 21, 2020

(65) Prior Publication Data

US 2021/0106101 A1    Apr. 15, 2021

Related U.S. Application Data

(63) Continuation of application No. 16/061,979, filed as application No. PCT/JP2015/086076 on Dec. 24, 2015, now Pat. No. 11,089,845.

(51) Int. Cl.
*B29C 39/14*     (2006.01)
*A44B 18/00*    (2006.01)
(Continued)

(52) U.S. Cl.
CPC ...... *A44B 18/0049* (2013.01); *A44B 18/0007* (2013.01); *A44B 18/0015* (2013.01);
(Continued)

(58) Field of Classification Search
CPC ....... B29C 39/14; B29C 39/148; B29C 43/22; B29C 43/222; B29C 43/52; B29C 43/26;
(Continued)

(56) References Cited

U.S. PATENT DOCUMENTS 4,083,667 A * 4/1978 Livingston .............. B29C 48/05
425/464
4,454,183 A    6/1984 Wollman
(Continued)

FOREIGN PATENT DOCUMENTS

CN    1232372 A    10/1999
CN    1307455 A    8/2001
(Continued)

OTHER PUBLICATIONS

U.S. Appl. No. 16/061,887, Final Office Action, Sep. 14, 2021, 12 pages.
(Continued)

*Primary Examiner* — Galen H Hauth
*Assistant Examiner* — Baileigh Kate Darnell
(74) *Attorney, Agent, or Firm* — Kilpatrick Townsend & Stockton LLP

(57) ABSTRACT

In this molded surface fastener, plural engaging elements having a stem portion and an engaging head portion formed integrally on the stem portion are standing on the base portion, at least one pawl portion having a pawl width dimension narrower than a width dimension at a boundary between the stem portion and the engaging head portion is protruded on an outer peripheral edge part of the engaging head portion, and a back surface of pawl of the pawl portion is formed at different angles with respect to a back surface of head portion of the engaging head portion. Such a molded surface fastener of the present invention has a substantial engaging force with respect to a female surface fastener and can make a texture of its surface comfortable.

3 Claims, 24 Drawing Sheets

(51) Int. Cl.
  *A61F 13/62* (2006.01)
  *B29C 43/22* (2006.01)
  *B29C 48/00* (2019.01)
  *B29C 69/02* (2006.01)
  *B29C 43/52* (2006.01)

(52) U.S. Cl.
  CPC ...... *A44B 18/0019* (2013.01); *A44B 18/0061* (2013.01); *A44B 18/0065* (2013.01); *A44B 18/0073* (2013.01); *A61F 13/625* (2013.01); *B29C 39/14* (2013.01); *B29C 39/148* (2013.01); *B29C 43/22* (2013.01); *B29C 43/222* (2013.01); *B29C 48/0011* (2019.02); *B29C 69/02* (2013.01); *B29C 43/52* (2013.01)

(58) Field of Classification Search
  CPC ........... B29C 48/0011; B29C 2043/461; A44B 18/0049; A44B 18/0007; A44B 18/0015; A44B 18/0019; A44B 18/0061; A44B 18/0065; A44B 18/0073; A44B 18/0076; B29L 2031/727
  See application file for complete search history.

(56) References Cited

U.S. PATENT DOCUMENTS

| | | | |
|---|---|---|---|
| 5,057,259 | A | 10/1991 | Parmelee |
| 5,785,784 | A | 7/1998 | Chesley et al. |
| 5,879,604 | A | 3/1999 | Melbye et al. |
| 5,913,482 | A | 6/1999 | Akeno et al. |
| 5,951,931 | A | 9/1999 | Murasaki et al. |
| 5,953,797 | A | 9/1999 | Provost et al. |
| 6,054,091 | A | 4/2000 | Miller et al. |
| 6,162,040 | A | 12/2000 | Clune |
| 6,287,665 | B1 | 9/2001 | Hammer |
| 6,627,133 | B1 | 9/2003 | Tuma |
| 7,052,638 | B2 | 5/2006 | Clarner et al. |
| 7,350,276 | B2 | 4/2008 | Minato et al. |
| 7,516,524 | B2 | 4/2009 | Provost et al. |
| 7,645,134 | B2 | 1/2010 | Jackson et al. |
| 7,807,081 | B2 | 10/2010 | Tuma |
| 8,784,722 | B2 | 7/2014 | Rocha |
| 8,819,902 | B2 | 9/2014 | Tuma |
| 8,881,369 | B2 | 11/2014 | Kirby et al. |
| 8,961,850 | B2 | 2/2015 | Wood et al. |
| 9,210,970 | B2 | 12/2015 | Collins et al. |
| 9,259,060 | B2 | 2/2016 | Cheng |
| 11,034,063 | B2 | 6/2021 | Bosser et al. |
| 11,363,857 | B2 | 6/2022 | Fukuhara et al. |
| 11,633,021 | B2 | 4/2023 | Takekawa et al. |
| 2001/0022409 | A1 | 9/2001 | Parellada et al. |
| 2002/0190418 | A1 | 12/2002 | Jens et al. |
| 2003/0085492 | A1 | 5/2003 | Schulte |
| 2003/0106188 | A1 | 6/2003 | Armela et al. |
| 2003/0131453 | A1 | 7/2003 | Clarner et al. |
| 2004/0031130 | A1 | 2/2004 | Clarner et al. |
| 2004/0031553 | A1 | 2/2004 | Berger |
| 2004/0074071 | A1 | 4/2004 | Golden et al. |
| 2004/0229739 | A1 | 11/2004 | Gorman et al. |
| 2005/0212170 | A1* | 9/2005 | Jahn .................. A44B 18/0049 264/210.2 |
| 2006/0096072 | A1 | 5/2006 | Minato et al. |
| 2007/0063375 | A1 | 3/2007 | Tuma |
| 2010/0306969 | A1 | 12/2010 | Seifert |
| 2013/0067702 | A1 | 3/2013 | Tuma |
| 2015/0010732 | A1 | 1/2015 | Tuma |
| 2015/0275941 | A1 | 10/2015 | Nisogi |
| 2017/0156451 | A1 | 6/2017 | Cheng |
| 2018/0360170 | A1 | 12/2018 | Fukuhara et al. |
| 2018/0368534 | A1 | 12/2018 | Fukuhara et al. |
| 2019/0008239 | A1 | 1/2019 | Fukuhara et al. |
| 2020/0390199 | A1 | 12/2020 | Michihata et al. |

FOREIGN PATENT DOCUMENTS

| | | |
|---|---|---|
| CN | 1336803 A | 2/2002 |
| CN | 1374050 A | 10/2002 |
| CN | 1644357 A | 7/2005 |
| CN | 1798509 A | 7/2006 |
| CN | 102984965 A | 3/2013 |
| CN | 104812262 A | 7/2015 |
| DE | 102007032622 A1 | 3/2008 |
| JP | 58-157404 | 9/1983 |
| JP | 2002-519078 A | 7/2002 |
| JP | 2002-262908 A | 9/2002 |
| JP | 2002-534194 A | 10/2002 |
| JP | 2004-357894 A | 12/2004 |
| JP | 2007-502229 A | 2/2007 |
| JP | 2007-528765 A | 10/2007 |
| JP | 2011-504776 A | 2/2011 |
| JP | 2011-182910 A | 9/2011 |
| JP | 2013-529974 A | 7/2013 |
| JP | 2015-504736 A | 2/2015 |
| WO | 1994/23610 A1 | 10/1994 |
| WO | 1998/14086 A1 | 4/1998 |
| WO | 2000/000053 A1 | 1/2000 |
| WO | 2000/041479 A2 | 7/2000 |
| WO | 2009/149909 A2 | 12/2009 |
| WO | 2011/163193 A1 | 12/2011 |
| WO | 2014/058717 A1 | 4/2014 |
| WO | 2017/110106 A1 | 6/2017 |

OTHER PUBLICATIONS

U.S. Appl. No. 16/062,038, Notice of Allowance, Sep. 24, 2021, 8 pages.
U.S. Appl. No. 16/807,251, Non-Final Office Action, Aug. 18, 2021, 9 pages.
U.S. Appl. No. 16/807,341, Non-Final Office Action, Aug. 20, 2021, 9 pages.
Decision of Refusal, Japanese Patent Application No. 2017-557728, Nov. 28, 2019, 9 pages.
Office Action, Taiwanese Patent Application No. 105140797, Sep. 28, 2017, 10 pages.
Office Action, Taiwanese Patent Application No. 105142192, Aug. 14, 2017, 19 pages.
Office Action, Taiwanese Patent Application No. 105143110, Aug. 23, 2017, 9 pages.
Office Action, Chinese Patent Application No. 201680075917.5, Dec. 31, 2021, 12 pages.
Office Action, Chinese Patent Application No. 201680075920.7, Dec. 30, 2020, 16 pages.
U.S. Appl. No. 16/061,887, Notice of Allowance, Feb. 5, 2021, 8 pages.
U.S. Appl. No. 16/062,038, Notice of Allowance, Jul. 22, 2021, 8 pages.
Decision of Refusal, Chinese Patent Application No. 201680075917.5, Jun. 23, 2021, 22 pages.
Office Action, Chinese Patent Application No. 201680075920.7, Jun. 28, 2021, 13 pages.
U.S. Appl. No. 16/061,887, Advisory Action, Nov. 30, 2020, 3 pages.
U.S. Appl. No. 16/061,887, Final Office Action, Sep. 18, 2020, 13 pages.
U.S. Appl. No. 16/061,887, Non-Final Office Action, Mar. 18, 2020, 13 pages.
U.S. Appl. No. 16/061,887, Restriction Requirement, Jan. 10, 2020, 9 pages.
U.S. Appl. No. 16/061,979, Corrected Notice of Allowance, Sep. 23, 2020, 5 pages.
U.S. Appl. No. 16/061,979, Non-Final Office Action, Mar. 19, 2020, 10 pages.
U.S. Appl. No. 16/061,979, Notice of Allowance, Sep. 14, 2020, 9 pages.
U.S. Appl. No. 16/061,979, Restriction Requirement, Jan. 10, 2020, 10 pages.

(56) References Cited

OTHER PUBLICATIONS

U.S. Appl. No. 16/061,979, Supplemental Notice of Allowability, Nov. 27, 2020, 2 pages.
U.S. Appl. No. 16/062,038, Advisory Action, Nov. 24, 2020, 3 pages.
U.S. Appl. No. 16/062,038, Final Office Action, Sep. 18, 2020, 13 pages.
U.S. Appl. No. 16/062,038, Non-Final Office Action, Apr. 29, 2020, 16 pages.
Chinese Patent Application No. 201580085530.3, Office Action, Apr. 2, 2020, 14 pages.
Chinese Patent Application No. 201680075917.5, Office Action, May 28, 2020, 12 pages.
Chinese Patent Application No. 201680075920.7, Office Action, Apr. 14, 2020, 16 pages.
European Patent Application No. 15911340.6, Extended European Search Report, Apr. 24, 2019, 8 pages.
European Patent Application No. 16878030.2, Extended European Search Report, Apr. 29, 2019, 8 pages.
European Patent Application No. 16878714.1, Extended European Search Report, Apr. 29, 2019, 9 pages.
Japanese Patent Application No. 2017-557590, Office Action, Jun. 4, 2019, 8 pages.
Japanese Patent Application No. 2017-557728, Office Action, Jun. 4, 2019, 10 pages.
Japanese Patent Application No. 2017-558167, Office Action, Jun. 11, 2019, 6 pages.
Korean Patent Application No. 10-2018-7015786, Office Action, Jan. 29, 2019, 20 pages.
Korean Patent Application No. 10-2018-7015787, Office Action, Jan. 29, 2019, 21 pages.
Korean Patent Application No. 10-2018-7015788, Office Action, Jan. 29, 2019, 17 pages.
PCT Patent Application No. PCT/JP2015/086076, International Search Report and Written Opinion, Mar. 15, 2016, 17 pages.
PCT Patent Application No. PCT/JP2016/072654, International Search Report and Written Opinion, Oct. 18, 2016, 20 pages.
PCT Patent Application No. PCT/JP2016/087982, International Search Report and Written Opinion, Mar. 14, 2017, 14 pages.
U.S. Appl. No. 16/061,887, Non-Final Office Action, Mar. 8, 2021, 13 pages.
U.S. Appl. No. 16/061,979, Notice of Allowance, Mar. 10, 2021, 10 pages.
U.S. Appl. No. 16/062,038, Non-Final Office Action, Mar. 10, 2021, 13 pages.
U.S. Appl. No. 17/465,044, Non-Final Office Action, Oct. 4, 2023, 14 pages.

* cited by examiner

MOLDING APPARATUS

This application is a continuation of U.S. patent application Ser. No. 16/061,979, which is incorporated by reference herein in its entirety.

TECHNICAL FIELD

The invention relates to a molded surface fastener in which a plurality of male engaging elements are standing on an upper surface of a flat plate-shaped base portion, a manufacturing method of the molded surface fastener and a molding apparatus used for manufacturing the molded surface fastener.

BACKGROUND ART

Conventionally, surface fastener products used by combining a female surface fastener having a plurality of loops and a male molded surface fastener capable of engaging and disengaging with the female surface fastener as a pair are known. Generally, a male molded surface fastener is formed such that a plurality of male engaging elements having a hook or a mushroom shape and the like are standing on an upper surface of a flat-plate shaped base portion.

Presently, surface fastener products having such a male molded surface fastener are widely used in a various kinds of goods. For example, it is often used for goods to be put on and taken off from a body such as a disposable diaper, a diaper cover for babies and infants, a supporter protecting joints of arms and legs, a corset for waist (belt for backache) and gloves.

Many kinds of molded surface fasteners used for a disposable diaper have been developed until now and they are disclosed in Japanese patent publication No. 2013-529974A (Patent Document 1) and U.S. patent publication No. 2013/0067702A (Patent Document 2), for example.

For example, as shown in FIGS. 44 and 45, a surface fastener 100 described in Patent Document 1 is formed such that a plurality of male engaging elements 102 are standing on a flat plate-shaped base portion 101. Each engaging element 102 has a frustum-shaped stem portion 103 and an engaging head portion 104 formed integrally on the stem portion 103. The engaging head portion 104 is formed so as to bulge from the stem portion 103 with a substantially equal volume in all directions.

In Patent Document 1, regarding at least some of the engaging elements 102, a bulging part 104*a* extending in only one direction of X direction or Y direction in the engaging head portion 104 is directed downward toward the base portion 101. According to Patent Document 1, the molded surface fastener 100 having engaging elements 102 as shown in FIGS. 44 and 45 can have a strong peeling strength when it is engaged with a surface fastener 100 having loop-shaped female engaging elements 102.

In Patent Document 2, as a molded surface fastener whose engaging and disengaging property is strengthened, a molded surface fastener having a plurality of male engaging elements 112, for example, as shown in FIGS. 46 and 47 is described. An engaging element 112 in Patent Document 2 has a stem portion 113 standing on a base portion 111 and an engaging head portion 114 formed integrally on the stem portion 113. A plurality of teeth 115 are provided on an outer peripheral edge part of the engaging head portion 114 so as to be a rotational symmetry about a center point. Further, the molded surface fastener in Patent Document 2 has an engaging element 112*a* in which the engaging head portion 114 is formed approximately parallel to the base portion 111 and an engaging element 112*b* in which the engaging head portion 114 is formed so as to roll back upward toward the outer peripheral edge.

In Patent Document 2, in a case of manufacturing the molded surface fastener, a method that a molten synthetic resin material is extruded between a molding roller and a pressure roller is adopted. In this case, a plurality of molding cavities having a shape corresponding to the engaging element 112 of the molded surface fastener are formed on an outer peripheral surface of the molding roller.

The synthetic resin material is extruded between such a molding roller and a pressure roller, thereby the base portion 111 is molded in a gap between the molding roller and the pressure roller. Further, the synthetic resin material is pushed into molding cavities of the molding roller by the pressure roller, thereby the engaging element 112 is molded integrally to the base portion 111. Then, after the synthetic resin material is cured while rotated together with the molding roller, the cured synthetic resin is picked up from the molding cavities of the molding roller and is peeled off from the molding roller. Thus the molded surface fastener in Patent Document 2 is manufactured.

Documents other than the above-mentioned Patent Documents 1 and 2, Japanese Patent Publication No. 2002-519078A (Patent Document 3) and Japanese Patent Publication No. 2002-262908A (Patent Document 4), for example, disclose a manufacturing method or a manufacturing apparatus of a surface fastener having a plurality of male engaging elements.

For example, in the manufacturing method described in Patent Document 3, firstly, a primary molding step for molding a primary molded body having a flat plate-shaped base portion, a stem portion standing on the base portion and a primary head portion formed integrally on the stem portion is conducted. Thereafter, a secondary molding step for molding the primary head portion so as to be an engaging head portion by extending the primary head portion flatly in a radial direction by making the primary molded body pass through a calender and pressing the primary head portion of the primary molded body is conducted.

In this case, a molding apparatus for the above-mentioned primary molding has a molding cylinder to be rotated, a press cylinder disposed opposing to the molding cylinder and setting a predetermined interval and an extrusion head providing a molten thermoplastic resin between the molding cylinder and the press cylinder. Further, the molding cylinder in Patent Document 3 has a cylinder-shaped outside screen and a cylinder-shaped inside screen contacting with an inner peripheral surface of the outside screen.

A plurality of column-shaped hollows molding the stem portion are formed on the outside screen of the molding cylinder. A plurality of column-shaped hollows molding the primary head portion are formed on the inside screen. Each hollow on the outside screen and each hollow on the inside screen are disposed aligning at a position corresponding to each other.

By using the molding apparatus having such a molding cylinder, the thermoplastic resin is provided from the extrusion head between the molding cylinder and the press cylinder while the molding cylinder and the press cylinder are rotated, thereby the primary molded body in which a plurality of engaging elements which has a stem portion and a primary head portion in which a depression is formed are standing on the base portion is molded.

Thereafter, the obtained primary molded body is passed through the calender and each primary head portion is made to be thin, thereby the molded surface fastener in Patent Document 3 in which a plurality of mushroom-shaped engaging elements are standing on the base portion is manufactured. The molded surface fastener manufactured in Patent Document 3 has a characteristic that a concave portion is formed on a center part of an upper surface in the engaging head portion of each engaging element.

On the other hand, a manufacturing apparatus of the molded surface fastener described in Patent Document 4 has a continuously-injecting apparatus molding an auxiliary molded body having a plurality of auxiliary molded element on a base portion and a heat press apparatus having a pair of upper and lower rollers disposed on a downstream side of the continuously-injecting apparatus and molding an engaging element by melting and deforming the auxiliary molded element.

The continuously-injecting apparatus has a cylindrical drum in which cavities for molding are formed on a peripheral surface part and rotating in one direction, an extrusion nozzle extruding the molten resin continuously toward the peripheral surface of the cylindrical drum and a take-up roller peeling off the auxiliary molded body molded on the peripheral surface of the cylindrical drum from the cylindrical drum. In this case, the cylindrical drum is a hollow-drum shape having a water cooling jacket which is a means of cooling inside and a peripheral surface has a function as a part of molded surface of the molded surface fastener.

Generally, the cylindrical drum is formed as column-shaped by laminating a plurality of ring-shaped (donut-shaped) plates having a necessary thickness in a rotating axis direction of the cylindrical drum. Further, predetermined cavities for molding are formed on a peripheral edge part of the predetermined ring-shaped plate at a predetermined pitch in a circumferential direction corresponding to a position of the plate by an electrical discharge machining or a laser processing.

By using the continuously-injecting apparatus, the molten resin material is extruded continuously from the extrusion nozzle toward the peripheral surface of the cylindrical drum, thereby the auxiliary molded body is molded continuously. Further, the auxiliary molded body is peeled off from the cylindrical drum via the take-up roller and conveyed to the heat press apparatus.

Thereafter, the auxiliary molded body conveyed to the heat press apparatus is introduced between a lower roll and an upper part heat pressing roll, thereby an auxiliary molded element of the auxiliary molded body is pressed from an upper side, then a flat and thin plate-shaped engaging head portion is molded. Thus, the molded surface fastener in Patent Document 4 in which a plurality of engaging elements having a cross-shaped post portion and a characteristic, approximately rectangular and thin plate-shaped engaging head portion are standing on the base portion is manufactured.

PRIOR ART DOCUMENTS

Patent Documents

Patent Document 1: Japanese Patent Publication No. 2013-529974A
Patent Document 2: U.S. Patent Publication No. 2013/0067702A
Patent Document 3: Japanese Patent Publication No. 2002-519078A
Patent Document 4: Japanese Patent Publication No. 2002-262908A

SUMMARY OF INVENTION

Problem to be Solved by the Invention

Normally, regarding the molded surface fastener used for goods which are put on a body such as the above-mentioned disposable diaper or diaper cover, it is required that an engaging strength (peeling strength) is enhanced so as an engaging and disengaging operation of a male surface fastener and a female surface fastener to be easy and both surface fasteners not to be separated easily even when a wearer moves in a state of engaging both surface fasteners. Further, depending on goods to be used, the molded surface fastener often contacts directly to a skin. Therefore, it is also desired to make a texture of the top surface side in which the male engaging elements of the molded surface fastener are disposed smooth so as to obtain soft tactile.

However, for example, in the molded surface fastener 100 having male engaging elements 102 in Patent Document 1 (see FIGS. 44 and 45), the engaging strength in an orthogonal direction to a bulging part 104a of the engaging head portion 104 is weak in comparison to a direction in which the bulging part 104a is directed downward.

In the molded surface fastener having male engaging elements 112 in Patent Document 2 (see FIGS. 46 and 47), since large concaves and convexes are formed in an outer peripheral edge part of the engaging head portion 114, certainly the engaging strength is expected to be enhanced, but the tactile can be significantly worsen. In addition, since a concave part is formed on an upper surface of each engaging head portion of the molded surface fastener having the male engaging elements in Patent Document 3, the texture of the molded surface fastener seems to be deteriorated, and moreover, the substantial engaging strength seems to be hard to be obtained.

In a case that the molded surface fastener is manufactured by using the molding apparatus described in Patent Document 4, since the cylindrical drum is formed by laminating a plurality of ring-shaped plates as mentioned above, small burrs may occur in the primary molded body at a boundary part of the adjacent ring-shaped plates. Moreover, since a position of the laminated ring-shaped plates are easy to misalign a little in the circumferential direction of the cylindrical drum, there is a possibility that a shape of the engaging element is affected. Therefore, the molding apparatus in Patent Document 4 becomes less used in manufacturing the molded surface fasteners to which a comfortable texture is required or the small size molded surface fasteners.

The present invention was made in light of the above-mentioned conventional problems. Its specific objective is to provide a molded surface fastener which has a substantial engaging strength (peeling strength) with respect to a female surface fastener and from which a comfortable texture can be stably obtained, and further provide a manufacturing method by which such a molded surface fastener can be stably manufactured and a molding apparatus used for manufacturing the molded surface fastener.

Means for Solving the Problem

To achieve the above objective, the molded surface fastener provided by the present invention is, as a basic structure, the one made of synthetic resin in which a plurality of male engaging elements are standing on an upper surface of a flat plate-shaped base portion and each engaging element has a stem portion standing on the base portion and an engaging head portion bulging from an upper end of the stem portion toward an outside and formed integrally on the stem portion, in which in at least a part of the engaging elements, at least one pawl portion having a pawl width dimension narrower than a width dimension at a boundary between the stem portion and the engaging head portion is protruded on an outer peripheral edge part of the engaging head portion and a back surface of pawl disposed opposing to the base portion of the pawl portion is formed at different angles with respect to a back surface of head portion extending from the boundary of the engaging head portion to an outside, as a most principal configuration.

In particular, it is preferable that the pawl portion of the molded surface fastener of the present invention is formed to slope or curve downward toward the base portion.

In the molded surface fastener of the present invention, it is preferable that a plurality of the pawl portions are provided with respect to one engaging head portion. In this case, it is preferable that a plurality of the pawl portions are disposed on the engaging head portion regularly. Further, a plurality of the pawl portions may be disposed on the engaging head portion irregularly.

Moreover, in the present invention, it is preferable that a plurality of the pawl portions are formed at different angles respectively. In addition, it is preferable that a plurality of the pawl portions are formed with different sizes respectively.

In the molded surface fastener in the present invention, it is preferable that an upper surface of pawl and the back surface of pawl of the pawl portion are formed to be a sloped surface or a curved surface declining toward a tip end.

It is preferable that the engaging head portion has a shape appearing a configuration similar to a cross section at the boundary in a plan view. It is preferable that the engaging head portion has a shape appearing a circle in a plan view.

In the molded surface fastener in the present invention, it is preferable that a base end part of the pawl portion has a pawl width dimension narrower than one third size of a width dimension of the boundary.

Further, it is preferable that a height dimension from the upper surface of the base portion in the engaging element is set to be 0.05 mm or more and 1.5 mm or less, a width dimension at the boundary is set to be 0.1 mm or more and 0.5 mm or less, a bulging length from the boundary in the engaging head portion is set to be 0.01 mm or more and 0.2 mm or less, and a pawl width dimension in the base end part of the pawl portion is set to be 0.01 mm or more and 0.1 mm or less.

Next, a manufacturing method of the molded surface fastener provided by the present invention is to manufacture a molded surface fastener made of synthetic resin in which a plurality of male engaging elements are standing on an upper surface of a flat plate-shaped base portion and each engaging element has a stem portion standing on the base portion and an engaging head portion bulging from an upper end of the stem portion toward an outside and formed integrally on the stem portion, including a primary molding step for molding a primary molded body having the base portion and a plurality of provisional elements standing on the base portion and a secondary molding step for molding the molded surface fastener by heating the provisional elements of the primary molded body and compressing the provisional elements from an upper side, and further including molding a primary stem portion erected from the base portion, a bulging portion bulging from an upper surface of the primary stem portion upward and a protruded portion protruding from the bulging portion to an outside of the primary stem portion as at least a part of the provisional elements in the primary molding step, and molding the stem portion and the engaging head portion as well as molding at least one pawl portion protruding on an outer peripheral edge part of the engaging head portion by compressing an upper end part of the provisional element having the bulging portion and the protruded portion in the secondary molding step, as a most principal configuration.

It is preferable that such a manufacturing method of the present invention includes, in the primary molding step, molding the primary molded body by using a die wheel which has an outer side cylindrical body on which a plurality of penetration holes penetrating from an outer peripheral surface to an inner peripheral surface are drilled and an inner side cylindrical body disposed closely contacting with an inner peripheral surface of the outer side cylindrical body, in which a plurality of concave portions are concaved on the outer peripheral surface of the inner side cylindrical body, and in which an outer peripheral edge of at least a part of the penetration holes in the inner peripheral surface of the outer side cylindrical body has a part overlapping with the concave portions of the inner side cylindrical body and a part closely contacting with the outer peripheral surface of the inner side cylindrical body.

Further, a manufacturing method of the present invention may include, in the primary molding step, molding the primary molded body by using a belt mechanism which has an outer side endless belt on which a plurality of penetration holes penetrating from an outer peripheral surface to an inner peripheral surface are drilled and an inner side endless belt disposed closely contacting with an inner peripheral surface of the outer side endless belt, in which a plurality of concave portions are concaved on the outer peripheral surface of the inner side endless belt, and in which an outer peripheral edge of at least a part of the penetration holes in the inner peripheral surface of the outer side endless belt has a part overlapping with the concave portion of the inner side endless belt and a part closely contacting with the outer peripheral surface of the inner side endless belt.

Further, it is preferable that the above-mentioned manufacturing method of the present invention includes molding the bulging portion and the protruded portion integrally on an upper surface of the primary stem portion so as to be a stick shape, a shape curving as a wave, or a polygon shape.

Next, the molding apparatus provided by the present invention has a die wheel driving rotationally in one direction and an extrusion nozzle extruding a molten synthetic resin material toward the die wheel, and molds a primary molded body having a flat plate-shaped base portion and a plurality of provisional elements standing on an upper surface of the base portion to manufacture the molded surface fastener, in which the die wheel has a concentric bicylindrical structure having an outer side cylindrical body and an inner side cylindrical body disposed closely contacting with an inner peripheral surface of the outer side cylindrical body, a plurality of penetration holes penetrating from an outer peripheral surface to an inner peripheral surface are drilled on the outer side cylindrical body, a plurality of concave portions to which the molten synthetic resin material can be flowed are concaved on the outer peripheral surface of the inner side cylindrical body, and an outer peripheral edge of at least a part of the penetration holes in the inner peripheral surface of the outer side cylindrical body has a part overlapping with the concave portion of the inner side cylindrical body and a part closely contacting with the outer peripheral surface of the inner side cylindrical body, as a most principal configuration.

The other molding apparatus provided by the present invention has a belt mechanism running rotationally in one direction and an extrusion nozzle extruding a molten synthetic resin material toward the belt mechanism, and molds a primary molded body having a flat plate-shaped base portion and a plurality of provisional elements standing on an upper surface of the base portion to manufacture the molded surface fastener, in which the belt mechanism has a double-belt structure having an outer side endless belt and an inner side endless belt disposed closely contacting with an inner peripheral surface of the outer side endless belt and rotating the outer side and inner side endless belts synchronically, a plurality of penetration holes penetrating from an outer peripheral surface to an inner peripheral surface are drilled in the outer side endless belt, a plurality of concave portions to which the molten synthetic resin material can be flowed are concaved on the outer peripheral surface of the inner side endless belt, and an outer peripheral edge of at least a part of the penetration holes in the inner peripheral surface of the outer side endless belt has a part overlapping with the concave portion of the inner side endless belt and a part closely contacting with the outer peripheral surface of the inner side endless belt, as a most principal configuration.

Further, in the above two molding apparatuses according to the present invention, it is preferable that the concave portion is a concave groove portion which has a linear shape or a shape curving as a wave. In this case, it is particularly preferable that a groove width of each concave groove portion is set to be 0.005 mm or more and 0.1 mm or less, and a groove depth of each concave groove portion is set to be 0.005 mm or more and 0.05 mm or less.

The concave portion may be concaved as a polygon shape.

Effects of the Invention

The molded surface fastener according to the present invention has a stem portion standing on a base portion and a plurality of male engaging elements having an engaging head portion bulging from an upper end of the stem portion toward an outside. In at least a part of the engaging elements (preferably all engaging elements), at least one pawl portion having a pawl width dimension narrower than a width dimension of a boundary in the engaging element is protruded on an outer peripheral edge part of each engaging head portion, and a back surface of pawl of the pawl portion is formed at different angles with respect to a back surface of head portion of the engaging head portion.

Here, the pawl width dimension means a dimension of the pawl portion in a direction orthogonal to a protruding direction of the pawl portion or a bulging direction of the engaging head portion and also orthogonal to an upper and lower direction (erecting direction of the stem portion) of the molded surface fastener. A width dimension of a boundary means a dimension of the boundary in arbitral one direction among directions (or a flat plane) orthogonal to the upper and lower direction (erecting direction of the stem portion) of the molded surface fastener. Particularly in the present invention, it means a dimension in a machine direction in a molding step of the molded surface fastener (MD: a flowing direction of the molded surface fastener) among directions orthogonal to the erecting direction of the stem portion. In the engaging element of the present invention, for example, in a case that a shape of a cross section at the boundary appears a circular shape in a plan view, the width dimension of the boundary is the same size as a diameter of the circular cross section at the boundary.

Each engaging element has a micro pawl portion as mentioned above, thereby, for example in a case that loops (engaging elements) of a female surface fastener is engaged with male engaging elements of the molded surface fastener according to the present invention, loops of the female surface fastener is easy to hook over the pawl portion and the loops of the female surface fastener can be hard to disengage from the engaging element of the present invention.

That is, in a state that the engaging element of the present invention is got into the loops of the female surface fastener and the molded surface fastener of the present invention and the female surface fastener are engaged, and for example in a case that the loops of the female surface fastener are to be disengaged from the engaging element of the present invention, the loops of the female surface fastener normally move as if sliding along the outer peripheral edge part of the engaging head portion in the engaging element of the present invention.

In this case, in the present invention, since a micro pawl portion having the above-mentioned back surface of pawl is protruded on the outer peripheral edge part of the engaging head portion, the loops of the female surface fastener is easy to hook over the outer peripheral edge part of the engaging head portion and becomes hard to disengage from the engaging element of the present invention.

Thus, in the present invention, an engaging strength (peeling strength) with respect to the female surface fastener of the molded surface fastener can be effectively enhanced by the micro pawl portion provided on the outer peripheral edge part of the engaging head portion. Therefore, in a case that the molded surface fastener of the present invention is used for goods, for example, such as a disposable diaper, even when various movements are done in a state that the molded surface fastener and the female surface fastener are engaged, the engaged state can be stably maintained.

Further, in the present invention, since the pawl portion enhancing the engaging strength is provided on the outer peripheral edge part of the engaging head portion with a micro size having the above-mentioned pawl width dimension, effects of the pawl portion on the tactile of the molded surface fastener can be limited. Therefore, by forming the engaging head portion of the engaging element to be, for example, a disc shape with a flat upper surface, smooth tactile or soft and flexible tactile can be easily obtained, which enables to provide a male molded surface fastener having a substantial engaging strength and comfortable texture of a top surface stably.

Particularly in the present invention, by forming the pawl portion so as to slope or curve downward toward the base portion, the loops of the female surface fastener can easily hook over the outer peripheral edge part of the engaging head portion. Thereby, the engaging strength (peeling strength) of the molded surface fastener can be more effectively enhanced.

In such a molded surface fastener in the present invention, by providing a plurality of pawl portions on one engaging head portion (engaging element), the engaging strength of the molded surface fastener can be more enhanced. Particularly in this case, a plurality of pawl portions are disposed on the engaging head portion regularly, or protruded from the engaging head portion with the same angle and the same size each other, thereby the engaging strength can be stably enhanced.

It should be noted that, in the present invention, a plurality of pawl portions may be disposed on the engaging head portion irregularly. By arranging a plurality of pawl portions randomly, for example, even in a case that the loops of the female surface fastener are formed randomly, the engaging strength of the molded surface fastener with respect to the female surface fastener can be effectively enhanced.

Further, in the molded surface fastener of the present invention, a plurality of pawl portions may be protruded from the engaging head portion at different angles, and also may be formed with different sizes. Also in these cases, the engaging strength of the molded surface fastener can be effectively enhanced.

In the molded surface fastener of the present invention, the upper surface of pawl and the back surface of pawl of the pawl portion are formed to be a sloped surface or a curved surface declining toward a tip end of the pawl. Thereby, the engaging strength of the molded surface fastener can be more enhanced and the texture of the molded surface fastener can be further improved.

Moreover, the engaging head portion of the engaging element has a shape appearing a configuration similar to a cross section at the boundary of the engaging element in a plan view. By such an engaging element, the engaging element can be easily and stably molded and the above-mentioned pawl portion can be stably provided on the engaging head portion.

Further, the engaging head portion of the engaging element has a shape appearing a circle in a plan view, thereby the texture of the molded surface fastener can be stably improved.

Particularly in the present invention, a base end part of the pawl portion has a pawl width dimension narrower than one third size, preferably one fifth size, more preferably one seventh size of a width dimension at the boundary of the engaging element. By having the pawl portion with such a size, the engaging strength of the molded surface fastener can be stably enhanced and a comfortable texture of the molded surface fastener can be stably obtained.

Further, a height dimension from an upper surface of the base portion in the engaging element is set to be 0.05 mm or more and 1.5 mm or less, a width dimension at the boundary of the engaging element is set to be 0.1 mm or more and 0.5 mm or less, a bulging length (bulging dimension) from the boundary part in the engaging head portion is set to be 0.01 mm or more and 0.2 mm or less and a pawl width dimension in the base end part of the pawl portion is set to be 0.01 mm or more and 0.1 mm or less. By the male molded surface fastener in which the engaging elements having such a size are formed, the engaging strength of the molded surface fastener can be effectively enhanced and a comfortable texture of the molded surface fastener can be stably obtained.

Next, a manufacturing method of the present invention for manufacturing the above-mentioned molded surface fastener includes a primary molding step for molding a primary molded body having a base portion and a plurality of provisional elements standing on the base portion and a secondary molding step for molding a molded surface fastener by heating the obtained provisional elements of the primary molded body and compressing the provisional elements from an upper side.

Particularly, in the primary molding step of the present invention, regarding at least a part of provisional elements (preferably all provisional elements), a primary stem portion erected from the base portion, a bulging portion bulging from an upper surface of the primary stem portion upward and a protruded portion protruding from the bulging portion to an outside of the primary stem portion are molded, and in the secondary molding step, a stem portion and an engaging head portion of the engaging element as well as at least one pawl portion protruding on the outer peripheral edge part of the engaging head portion are molded by compressing an upper end part of the provisional element in which the bulging portion and the protruded portion are formed. Thereby, the molded surface fastener of the present invention as described above can be efficiently and stably manufactured.

In such a manufacturing method of the present invention, in the primary molding step, a die wheel which has an outer side cylindrical body in which a plurality of penetration holes penetrating from an outer peripheral surface to an inner peripheral surface are drilled and an inner side cylindrical body disposed closely contacting with an inner peripheral surface of the outer side cylindrical body, in which a plurality of concave portions are concaved on the outer peripheral surface of the inner side cylindrical body, and in which an outer peripheral edge of at least a part of the penetration holes (preferably all penetration holes) in the inner peripheral surface of the outer side cylindrical body has a part overlapping with the concave portion of the inner side cylindrical body and a part closely contacting with the outer peripheral surface of the inner side cylindrical body is used. Thereby, the primary molded body having a plurality of provisional elements can be efficiently and stably formed and a molding apparatus of the primary molded body can be formed in a simple structure.

Further, in the manufacturing method of the present invention, in the primary molding step, a belt mechanism which has an outer side endless belt in which a plurality of penetration holes penetrating from an outer peripheral surface to an inner peripheral surface are drilled and an inner side endless belt disposed closely contacting with an inner peripheral surface of the outer side endless belt, in which a plurality of concave portions are concaved on the outer peripheral surface of the inner side endless belt, and in which an outer peripheral edge of at least a part of the penetration holes (preferably all penetration holes) in the inner peripheral surface of the outer side endless belt has a part overlapping with the concave portion of the inner side endless belt and a part closely contacting with the outer peripheral surface of the inner side endless belt may be used. Also in this case, the primary molded body having a plurality of provisional elements can be efficiently and stably formed and deformation can be hard to remain in the primary molded body.

Further, in the manufacturing method of the present invention, the bulging portion and the protruded portion of each provisional element are molded integrally on an upper surface of the primary stem portion so as to be a stick shape, a shape curving as a wave, or a polygon shape, thereby the protruded portion can be easily and stably formed. Thereafter, the secondary molding step is conducted on the obtained primary molded body, thereby the engaging element having a micro pawl portion, which is a characteristics of the present invention, can be stably molded.

Next, the molding apparatus of the present invention has a die wheel driving rotationally in one direction and an extrusion nozzle extruding a molten synthetic resin material toward the die wheel. The die wheel has a concentric bicylindrical structure having an outer side cylindrical body and an inner side cylindrical body disposed closely contacting with an inner peripheral surface of the outer side cylindrical body. Further, a plurality of penetration holes penetrating from an outer peripheral surface to an inner peripheral surface are drilled on the outer side cylindrical body, and a plurality of concave portions to which the molten synthetic resin material can be flowed are concaved on the outer peripheral surface of the inner side cylindrical body. Particularly in the present invention, an outer peripheral edge of at least a part of the penetration holes in the inner peripheral surface of the outer side cylindrical body has a part overlapping with the concave portion of the inner side cylindrical body and a part closely contacting with the outer peripheral surface of the inner side cylindrical body.

Such a molding apparatus of the present invention can be formed in a simple structure, and can mold the primary molded body in which a plurality of provisional elements are standing on an upper surface of the flat plate-shaped base portion stably and efficiently. Particularly, by the above molding apparatus, small burrs occurred in the primary molded body can be effectively prevented, and even in a case that the provisional element is small, the provisional element having at least one protruded portion bulging from the primary stem portion to an outside can be stably molded.

The other molding apparatus in the present invention has a belt mechanism running rotationally in one direction and an extrusion nozzle extruding a molten synthetic resin material toward the belt mechanism. The belt mechanism has a double-belt structure having an outer side endless belt and an inner side endless belt disposed closely contacting with an inner peripheral surface of the outer side endless belt and rotating the outside and inner side endless belts synchronically. Further, a plurality of penetration holes penetrating from an outer peripheral surface to an inner peripheral surface are drilled on the outer side endless belt, a plurality of concave portions to which the molten synthetic resin material can be flowed are concaved on the outer peripheral surface of the inner side endless belt. Particularly in the present invention, an outer peripheral edge of at least a part of the penetration holes in the inner peripheral surface of the outer side endless belt has a part overlapping with the concave portion of the inner side endless belt and a part closely contacting with the outer peripheral surface of the inner side endless belt.

Also by such a molding apparatus of the present invention, the primary molded body in which a plurality of provisional elements are standing on the upper surface of the flat plate-shaped base portion can be stably and efficiently molded and deformation can be hard to remain in the primary molded body. Particularly, by the above molding apparatus, small burrs occurred in the primary molded body can be effectively prevented and even in a case that the provisional element is small, the provisional element having at least one protruded portion bulging from the primary stem portion to an outside can be stably molded.

In the above two molding apparatuses according to the present invention, a concave groove portion which has a linear shape or a shape curving as a wave is formed on the outer peripheral surface of the inner side cylindrical body or the inner side endless belt as the concave portion. Particularly in this case, a groove width of each concave groove portion is set to be 0.005 mm or more and 0.1 mm or less, and a groove depth of each concave groove portion is set to be 0.005 mm or more and 0.05 mm or less. Due to the above, the protruded portion can be stably provided on each provisional element of the primary molded body and the primary molded body by which the above-mentioned molded surface fastener of the present invention can be obtained can be efficiently molded.

In the present invention, a polygon-shaped concave portion may be concaved on the outer peripheral surface of the inner side cylindrical body or the inner side endless belt. Also due to this, the protruded portion can be stably provided in each provisional element of the primary molded body and the primary molded body in which the above-mentioned molded surface fastener of the present invention can be obtained can be efficiently molded.

DESCRIPTION OF EMBODIMENT

Hereinafter, preferred embodiments of the present invention are described in detail with Embodiments referring to drawings. It should be noted that the present invention is not limited thereto, and various changes can be made as long as they have a substantially same structure and same functional effects. For example, in the Embodiments below, a number, a disposing position and a forming density of male engaging element disposed on a base portion of a molded surface fastener is not limited in particular, and can be changed arbitrarily.

Embodiment 1

Figure 1:
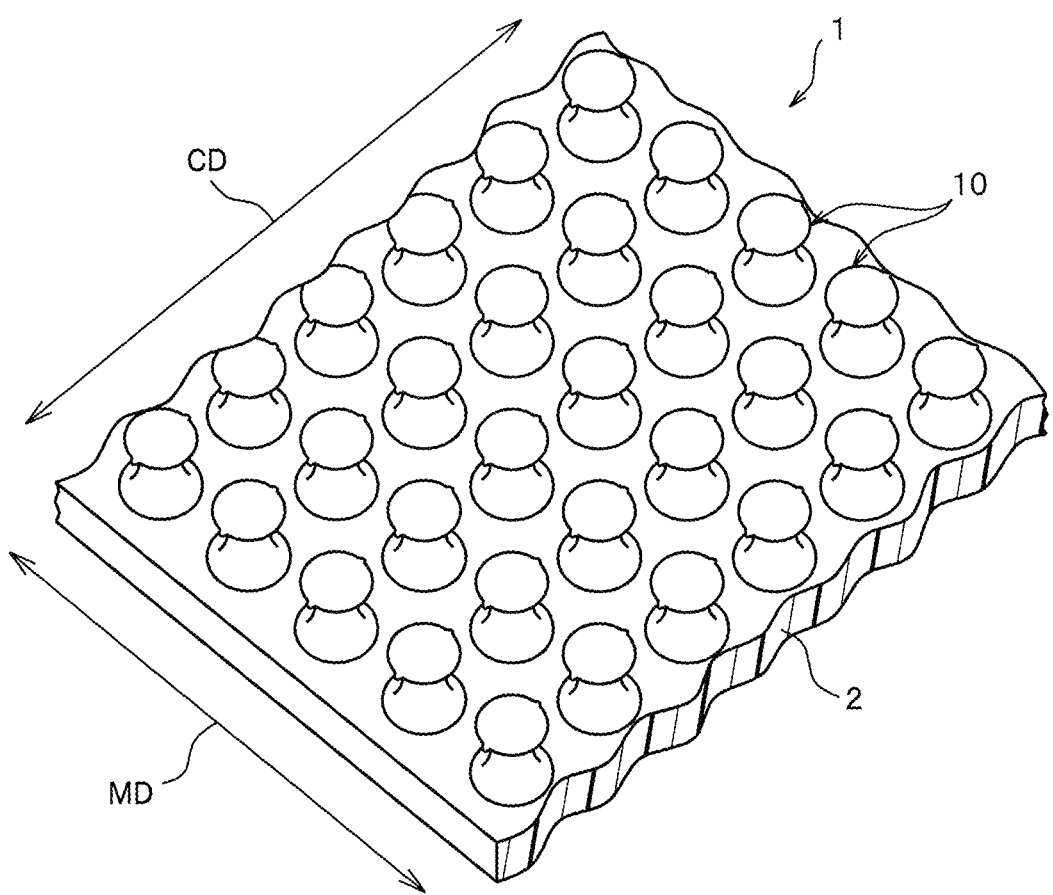
FIG. 1 is a perspective view illustrating a molded surface fastener according to Embodiment 1 of the invention.
Figure 2:
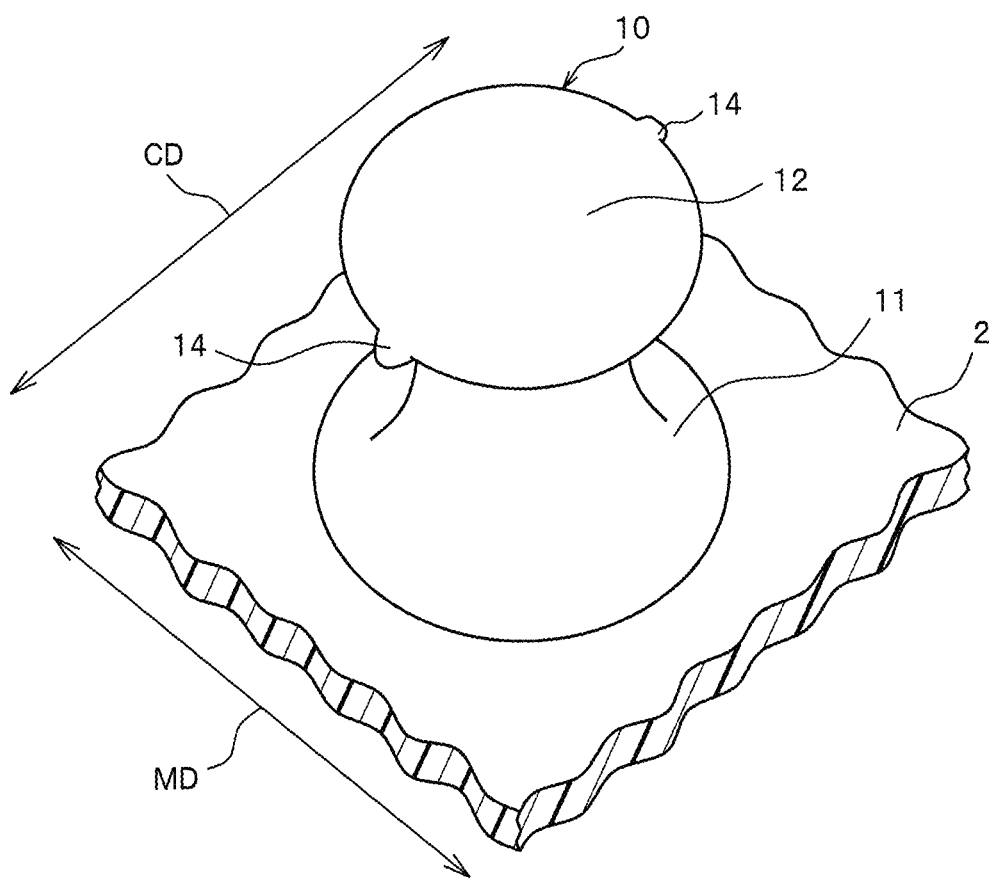
FIG. 2 is a perspective view illustrating an engaging element of the molded surface fastener.
Figure 3:
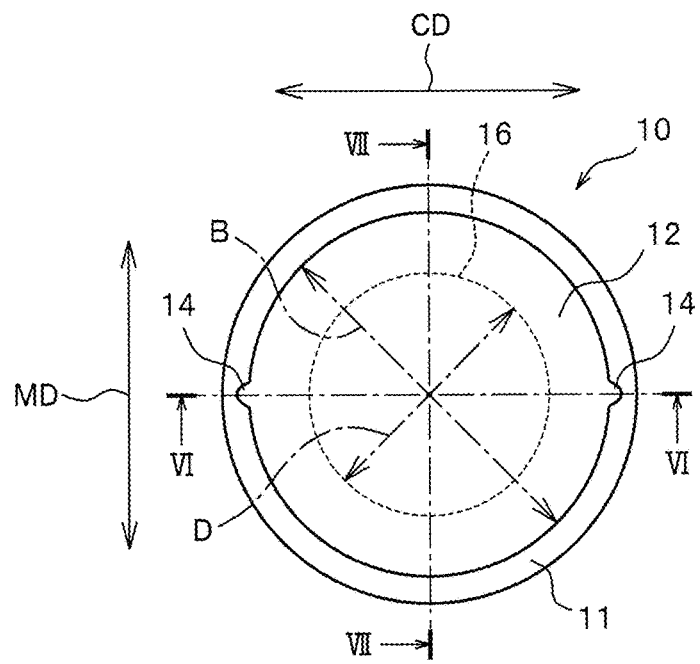
FIG. 3 is a plan view illustrating only the engaging element.
Figure 4:
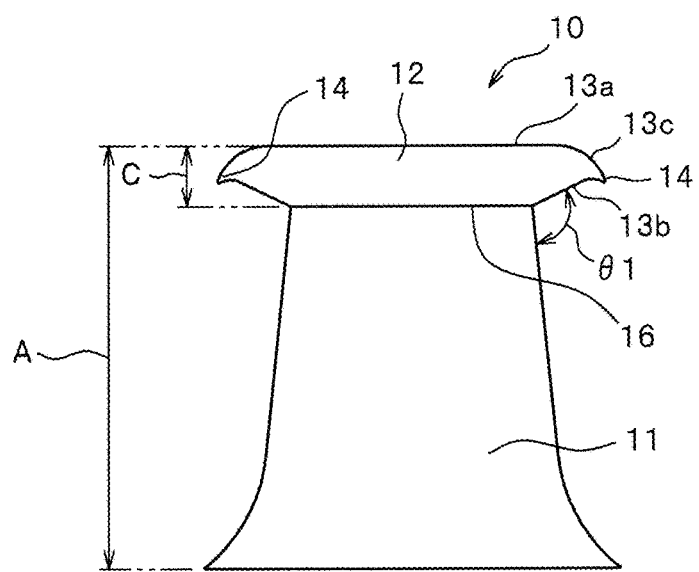
FIG. 4 is a front view viewing only the engaging element from a front and rear direction (machine direction: MD) of the molded surface fastener.
Figure 5:
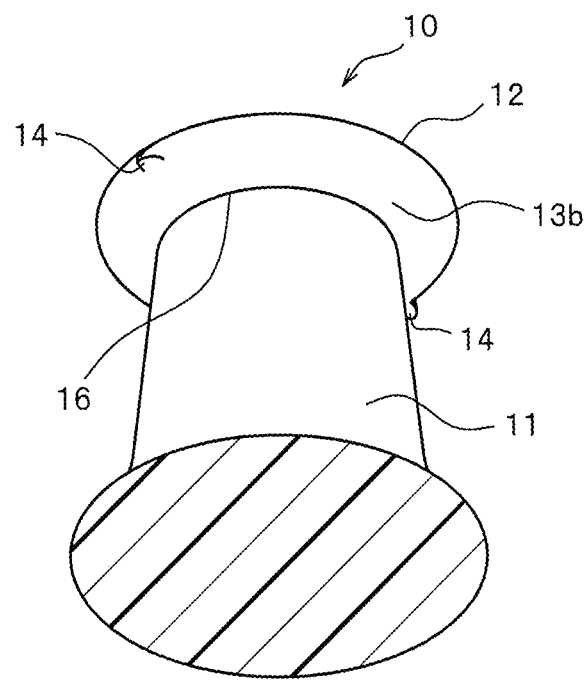
FIG. 5 is a perspective view viewing only the engaging element up diagonally from a base portion side.
Figure 6:
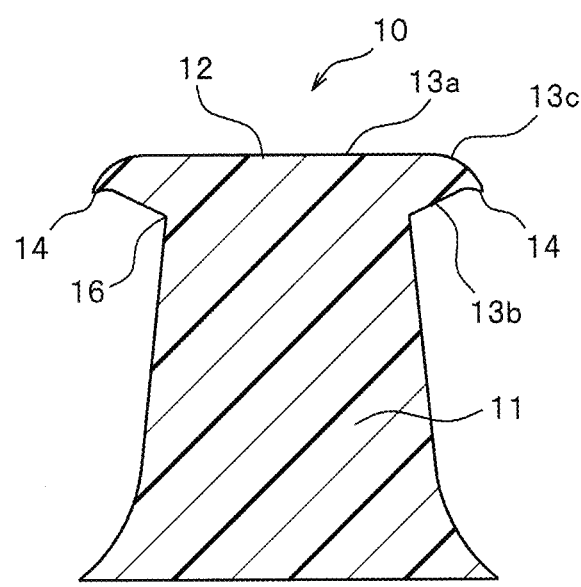
FIG. 6 is a cross-sectional view in VI-VI line shown in FIG. 3.
Figure 7:
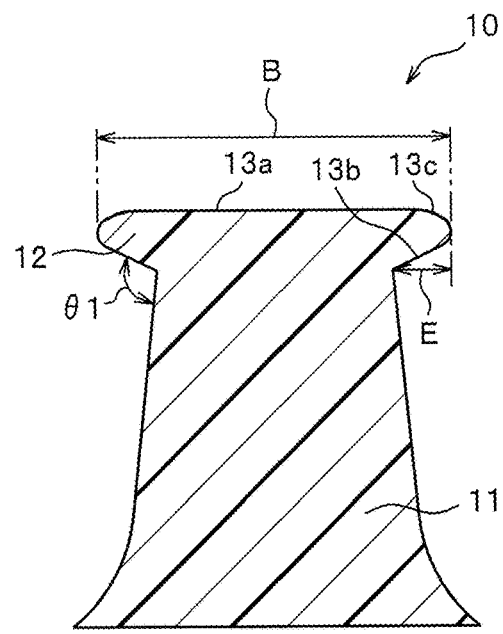
FIG. 7 is a cross-sectional view in VII-VII line shown in FIG. 3.
Figure 8:
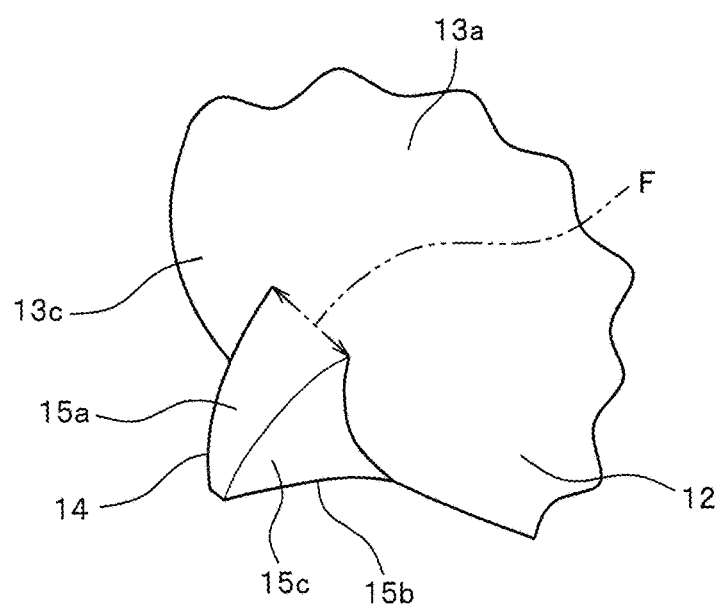
FIG. 8 is an enlarged perspective view illustrating a pawl portion disposed in the engaging element enlarged.
Figure 9:
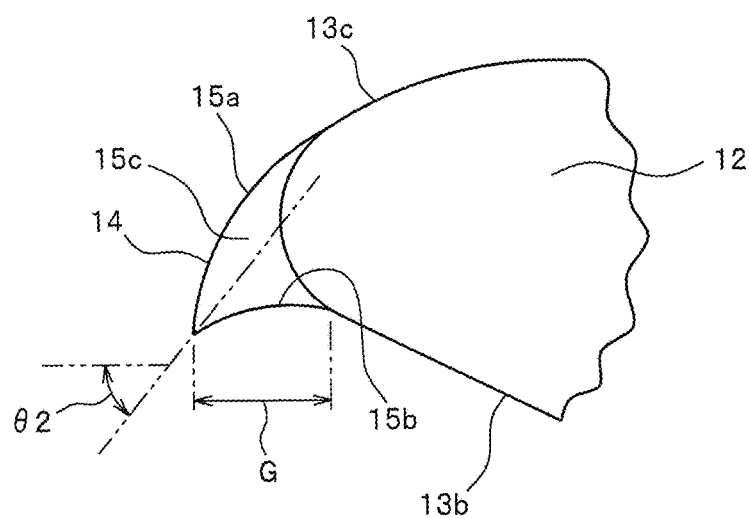
FIG. 9 is a front view viewing the pawl portion from a front and rear direction (MD) of the molded surface fastener enlarged.

FIG. 1 is a perspective view illustrating a molded surface fastener according to Embodiment 1 of the invention. FIGS. 2-5 are views viewing an engaging element of the molded surface fastener from various directions. FIGS. 6 and 7 are cross-sectional views of the engaging element. FIGS. 8 and 9 are enlarged views illustrating a pawl portion disposed in the engaging element enlarged.

It should be noted that, in the following explanation, a front and rear direction regarding a molded surface fastener and a primary molded body means a length direction of a molded surface fastener and a primary molded body molded long as described later, and also means a direction along a machine direction (M direction or MD) in which a molded surface fastener or a primary molded body flow in a manufacturing step of the molded surface fastener.

A left and right direction means a width direction orthogonal to a length direction and along an upper surface (or a lower surface) of the base portion of the molded surface fastener. In this case, the left and right direction and the width direction can be also referred to as a crossing direction (C direction or CD) orthogonal to the machine direction (MD). An upper and lower direction (thickness direction) means a height direction orthogonal to the length direction and orthogonal to an upper surface (or lower surface) of the base portion of the molded surface fastener.

The molded surface fastener 1 of Embodiment 1 shown in FIG. 1 is manufactured by molding a thermoplastic resin using a manufacturing apparatus 40 having a molding apparatus 50 and a heat press apparatus 70, as described later. The molded surface fastener 1 is formed as sheet-shaped which is long in a machine direction of the manufacturing apparatus 40 and has a rectangular shape in a plan view. It should be noted that a length dimension and a width dimension of the molded surface fastener 1 of the present invention are not limited in particular, and it can be arbitrarily changed by cutting the molded surface fastener 1. The molded surface fastener 1 may have a shape other than a rectangular shape in a plan view.

Further, a kind of synthetic resin forming the molded surface fastener 1 is not also limited in particular. However, for example, such thermoplastic resins as polypropylene, polyester, nylon, polybutylene terephthalate, or a copolymer of these can be adopted as a material of the molded surface fastener 1. In Embodiment 1, the molded surface fastener 1 is formed of polypropylene.

The molded surface fastener 1 of Embodiment 1 has a thin plate-shaped base portion 2 and a plurality of engaging elements 10 erected from an upper surface of the base portion 2 vertically. The base portion 2 is formed by having a predetermined thickness, and the upper surface and a lower surface of the base portion 2 are formed flat and parallel to each other.

A plurality of engaging elements 10 are disposed in line along a machine direction (MD) and a crossing direction (CD). It should be noted that, in the present invention, an arranging position of the engaging elements 10 are not limited, as described above. For example, a plurality of engaging elements 10 may be in line on the base portion 2 with a zigzag-shaped arranging pattern or with the other pattern, and also may be provided on the base portion 2 randomly.

Each engaging element 10 in Embodiment 1 has a stem portion 11 standing on the base portion 2, a disc- or dish-shaped engaging head portion 12 formed by bulging from a whole periphery of an upper end of the stem portion 11 toward an outside and two micro pawl portions 14 protruded on an outer peripheral edge part of the engaging head portion 12, respectively.

The stem portion 11 of the engaging element 10 is standing vertically on the base portion 2, and has a frustum of cone shape in which a cross sectional area orthogonal to the upper and lower direction gradually increases as it is close to the base portion 2. In particular, a lower end part of the stem portion 11 in Embodiment 1 is formed curving so as to enlarge the outer peripheral surface downward. It should be noted that, in the present invention, a shape of the stem portion 11 is not limited to a frustum of cone shape, and for example, it may be a truncated pyramid shape such as a truncated square pyramid, a columnar shape, or a prism shape such as a quadrangular prism.

The engaging head portion 12 of the engaging element 10 has a disc shape and formed integrally on the stem portion 11 via a boundary 16. Particularly, the engaging head portion 12 in Embodiment 1 has a shape appearing a circle in a plan view viewing the engaging element 10 from the upper side. The circular shape of the engaging head portion 12 in a plan view is similar with a circular shape of a cross section orthogonal to the upper and lower direction at the boundary 16 of the engaging element 10.

It should be noted that, the similarity referred in the specification includes not only a case of congruence that when enlarging or reducing a size of a scale of one shape so as to correspond to a scale of the other shape and overlapping both shapes, they totally correspond, but also a case of overlapping with an area of 85% or more, preferably with an area of 90% or more.

Particularly in this case, the engaging head portion 12 is formed so as to have a diameter of more than 1.0 times and 3.0 times or less, preferably 1.3 times or more and 2.0 times or less with respect to a diameter D of the circular cross section at the boundary 16 of the engaging element 10 in a plan view of the engaging element 10. It should be noted that, in a case that the engaging head portion appears a polygon in a plan view, the engaging head portion is formed so as a length of one corresponding side to be more than 1.0 times and 3.0 times or less, preferably 1.3 times or more and 2.0 times or less with respect to an arbitral side of the polygonal cross section at the boundary of the engaging element.

The engaging head portion 12 of Embodiment 1 has a flat top end surface of head portion 13a disposed parallel to the upper surface of the base portion 2. Further, a donut-shaped back surface of head portion 13b extending flatly from the boundary 16 with the stem portion 11 toward an outside is disposed on an opposite side of the top end surface of head portion 13a so as to oppose to the base portion 2. Moreover, a curved surface-shaped outer peripheral side surface 13c is disposed from the outer periphery of the top end surface of head portion 13a to the back surface of head portion 13b.

It should be noted that, in the present invention, a shape of the engaging head portion 12 may have a shape other than a circle corresponding to a shape of the cross section of the stem portion 11 in a plan view. The engaging head portion 12 does not need to bulge from the whole periphery of the upper end of the stem portion 11. Further, in a plan view of the molded surface fastener 1, a central position of the engaging head portion 12 in one engaging element 10 and a central position in a cross section (cross section of the boundary 16) of the upper end of the stem portion 11 may be displaced each other.

Each engaging element 10 of Embodiment 1 has two pawl portions 14 protruding from the outer peripheral side surface 13c of the engaging head portion 12 toward an outside. Two pawl portions 14 of each engaging element 10 protrudes from the outer peripheral side surface 13c of the engaging head portion 12 in a direction extending radially about a center of the engaging head portion 12 along a radial direction of the engaging head portion 12 appearing a circular shape in a plan view so as to be arranged regularly with respect to one engaging head portion 12. Particularly, in a case of Embodiment 1, in all the engaging elements 10, two pawl portions 14 protrudes in an opposing direction each other from the outer peripheral side surface 13c of the engaging head portion 12 along the left and right direction (C direction) so as to be in a point-symmetrical position relationship each other in a plan view of the engaging element 10.

Each pawl portion 14 has a shape hanging downward toward a tip end as a claw of birds, as showing the enlarged views in FIGS. 8 and 9. Each pawl portion 14 has an upper surface of pawl 15a declining toward the tip end, a back surface (lower surface) of pawl 15b disposed opposing to the base portion 2 and a pair of side wall surfaces 15c disposed between the upper surface of pawl 15a and the back surface of pawl 15b.

In this case, at a base end part linking to the engaging head portion 12 of the pawl portion 14, a pawl width dimension F (see FIG. 8) between a pair of side wall surfaces 15c of the pawl portion 14 is set to be one third or less of a dimension (width dimension) of M direction (MD) at the boundary 16 of the engaging element 10, preferably one fifth or less, further preferably one seventh or less. Each pawl portion 14 is formed having such a pawl width dimension F, thereby the pawl portion 14 contributing to an improvement of the engaging strength of the molded surface fastener 1 can be provided at the outer peripheral edge part of the engaging head portion 12 stably and an effect which the pawl portion 14 gives on the tactile of the molded surface fastener 1 can be limited, as described later.

It should be noted that, in a case of Embodiment 1, since the shape of the boundary 16 of the engaging element 10 in a plan view is a circle, the dimension of M direction at the boundary 16 becomes equal to the dimension in diameter D at the boundary 16. Also in a case that the shape of the boundary 16 of the engaging element 10 in a plan view is a polygon such as a square, for example, it is preferable that the pawl width dimension F between a pair of side wall surfaces 15c of the pawl portion 14 is set to be one third or less of a dimension in M direction at the boundary 16 of the engaging element 10, preferably one fourth or less.

Further, in the pawl portion 14 in Embodiment 1, a pawl width dimension F between a pair of side wall surfaces 15c decreases from the base end part of the pawl portion 14 toward a pawl tip end, and a pawl height dimension between the upper surface of pawl 15a and the back surface of pawl 15b has a shape decreasing from the base end part of the pawl portion 14 toward the pawl tip end.

Particularly in Embodiment 1, the upper surface of pawl 15a of the pawl portion 14 is formed as a curved surface declining toward the tip end. The back surface of pawl 15b of the pawl portion 14 is formed, as shown in FIG. 9, facing to a lower direction than the back surface of head portion 13b of the engaging head portion 12 and also formed as a curved surface curving as a concaved shape. That is, an inclination angle (for example, an angle sloping with respect to a horizontal surface parallel to the upper surface of the base portion) is different between the back surface of pawl 15b of the pawl portion 14 and the back surface of head portion 13b of the engaging head portion 12.

The pawl portion 14 is formed as above, thereby the engaging strength of the molded surface fastener 1 can be effectively enhanced and a comfortable texture of the upper surface of the molded surface fastener 1 can be stably obtained. It should be noted that, in the present invention, the upper surface of pawl 15a and the back surface of pawl 15b of the pawl portion 14 may be formed not as a curved surface, but as a flat surface.

In Embodiment 1, specific sizes of each engaging element 10 are set to be as follows.

For example, a height dimension A of the engaging element 10 from the upper surface of the base portion 2 in the upper and lower direction is set to be 0.05 mm or more and 1.5 mm or less, preferably 0.2 mm or more and 1.0 mm or less. A diameter B of the engaging head portion 12 in a plan view of the engaging head portion 12 is set to be 0.2 mm or more and 0.6 mm or less. It should be noted that, in a case that the engaging head portion appears a polygon shape in a plan view, for example, a dimension of the engaging head portion in M direction in a plan view of the engaging head portion is set to be 0.2 mm or more and 0.6 mm or less.

A height dimension C of the engaging head portion 12 in the engaging element 10 (that is, a height dimension from the boundary 16 of the engaging element 10 to the upper end of the engaging head portion 12) is set to be 0.01 mm or more and 0.1 mm or less. A diameter D at the boundary 16 of the engaging element 10 is set to be 0.1 mm or more and 0.5 mm or less. In a case that the boundary appears as a polygon shape in a plan view, the dimension of the boundary in M direction is set to be 0.1 mm or more and 0.5 mm or less.

A bulging dimension (bulging length) from a position of the boundary 16 of the engaging element 10 to a most outer edge position of the engaging head portion 12 in the engaging head portion 12 is set to be 0.01 mm or more and 0.2 mm or less, preferably 0.02 mm or more and 0.1 mm or less. A bulging angle θ1 formed by the outer peripheral side surface 13c of the stem portion 11 and the back surface of head portion 13b of the engaging head portion 12 in the engaging element 10 is set to be 90° or more and 140° or less.

A pawl width dimension F between a pair of side wall surfaces 15c at the base end part of the pawl portion 14 is set to be 0.01 mm or more and 0.10 mm or less, preferably 0.03 mm or more and 0.08 mm or less. A pawl length dimension G from a boundary position between the back surface of head portion 13b of the engaging head portion 12 and the back surface of pawl 15b of the pawl portion 14 to the tip end position of the pawl portion 14 is set to be 0.01 mm or more and 0.04 mm or less. A pawl protruding angle θ2 which becomes an inclination angle of an imaginary line connecting an intermediate position between the upper and lower surfaces at the base end part of the pawl portion 14 and a tip end of the pawl with respect to a horizontal surface parallel to the upper surface of the base portion 2 is set to be more than 0° and 90° or less.

Figure 10:
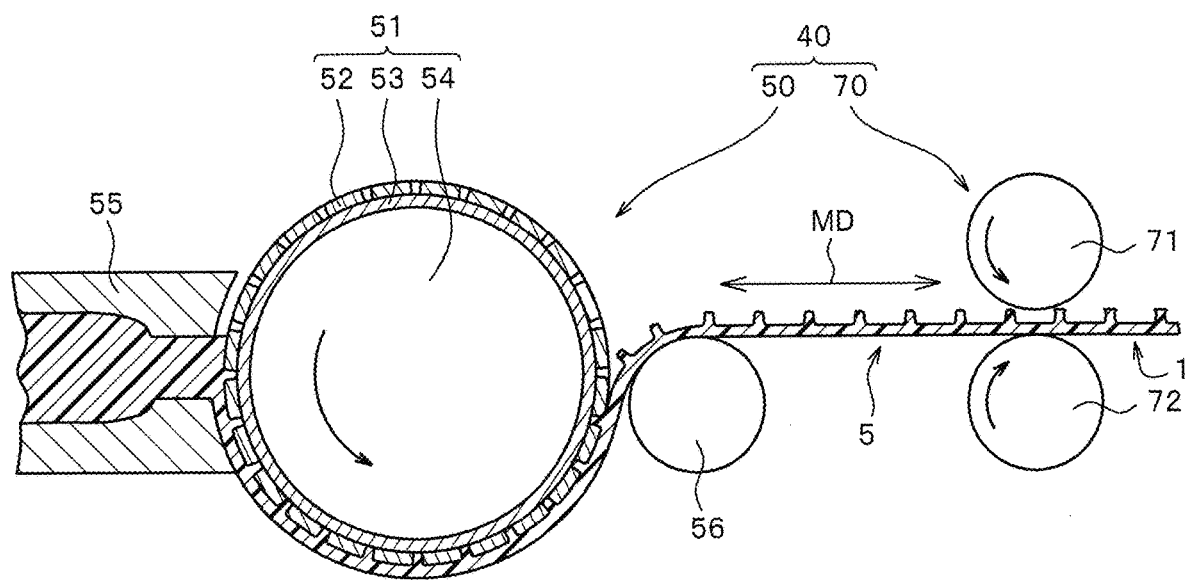
FIG. 10 is a schematic view illustrating a manufacturing apparatus of the molded surface fastener schematically.

The molded surface fastener 1 of Embodiment 1 having the above structure is manufactured by using a manufacturing apparatus 40 as shown in FIG. 10.

The manufacturing apparatus 40 has a molding apparatus 50 conducting a primary molding step and a heat press apparatus 70 heating and pressing the primary molded body 5 molded in the primary molding step.

The molding apparatus 50 of Embodiment 1 has a die wheel 51 which rotates drivingly in one direction (in a counterclockwise direction in Figures), an extrusion nozzle 55 which is disposed opposing to a circumferential surface of the die wheel 51 and extruding a molten synthetic resin material continuously and a pickup roller 56 which is disposed at a downstream side in a rotating direction of the die wheel 51 compared to the extrusion nozzle 55.

The die wheel 51 has a cylinder-shaped outer side cylindrical body (outer side sleeve) 52 and a cylinder-shaped inner side cylindrical body (inner side sleeve) 53 disposed closely contacting to an inside of the outer side cylindrical body 52, which become a mold, and a rotational driving roller 54 rotating the outer side and inner side cylindrical bodies 52, 53 in one direction. In this case, the die wheel 51 has a bicylindrical structure in which the outer side cylindrical body 52 and the inner side cylindrical body 53 are disposed rotatably and concentrically. A cooling jacket not shown in Figures distributing a liquid coolant is provided inside the rotational driving roller 54 and can cool the primary molded body 5 molded on the peripheral surface of the die wheel 51 efficiently.

Figure 11:
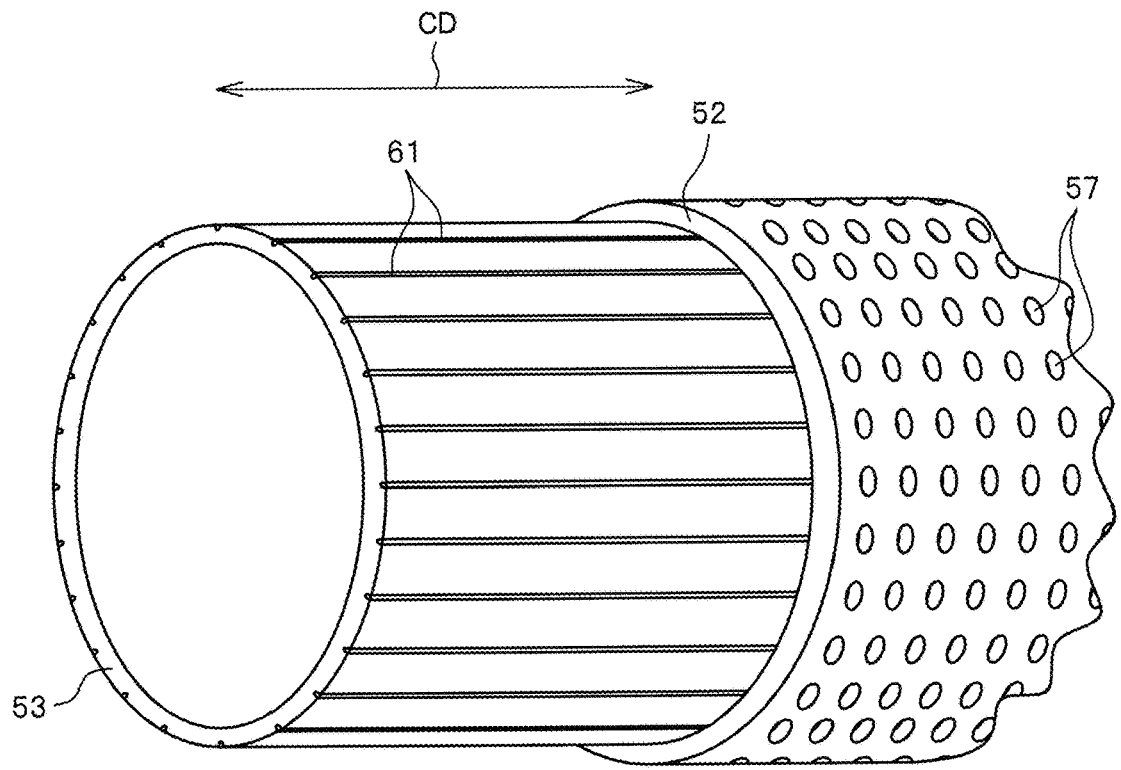
FIG. 11 is a perspective view illustrating an outer side cylindrical body and an inner side cylindrical body of a molding apparatus schematically.
Figure 12:
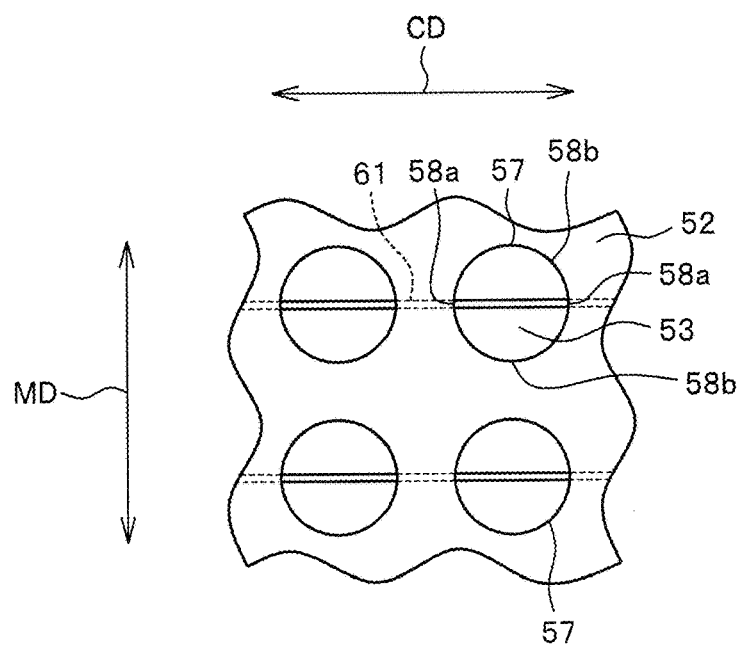
FIG. 12 is a main part schematic view illustrating a position relationship between penetration holes formed on an outer side cylindrical body and concave groove portions provided on an inner side cylindrical body.
Figure 13:
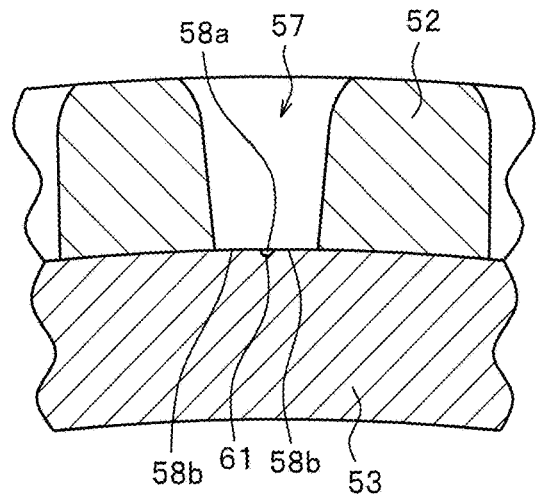
FIG. 13 is a cross-sectional view illustrating a cross section of the outer side cylindrical body and the inner side cylindrical body.
Figure 14:
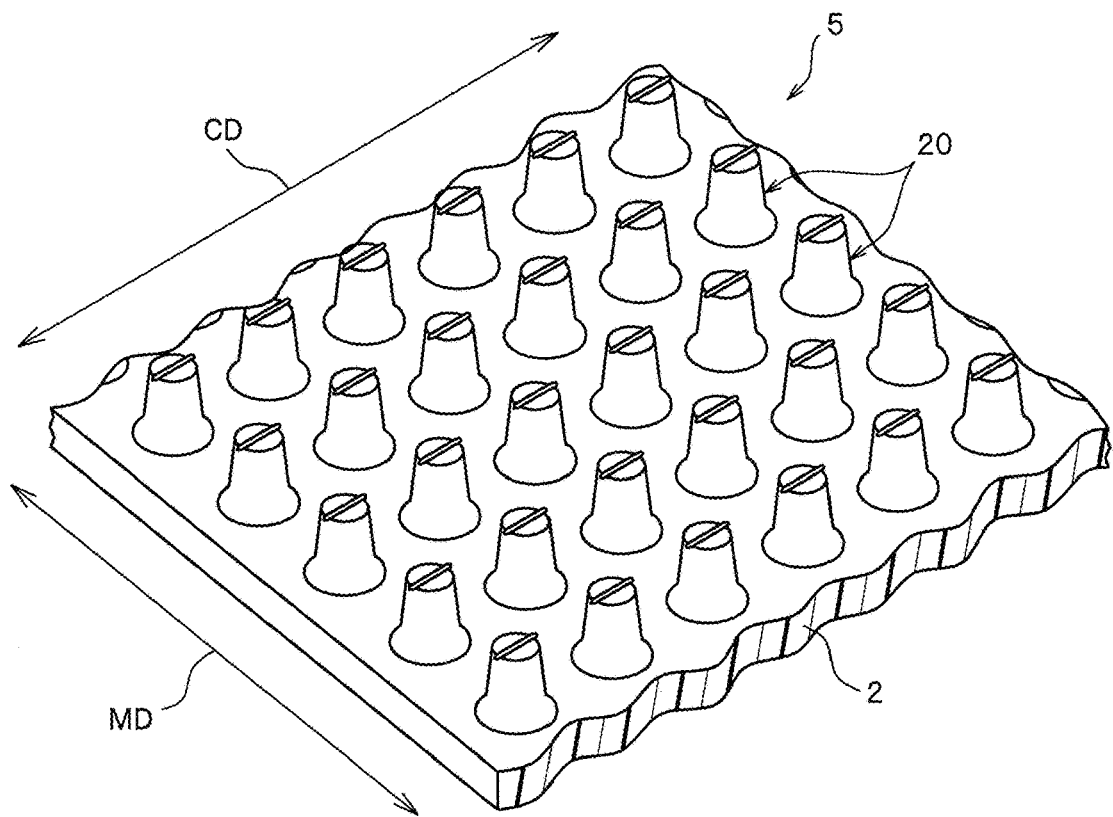
FIG. 14 is a perspective view illustrating a primary molded body obtained by a molding apparatus.
Figure 15:
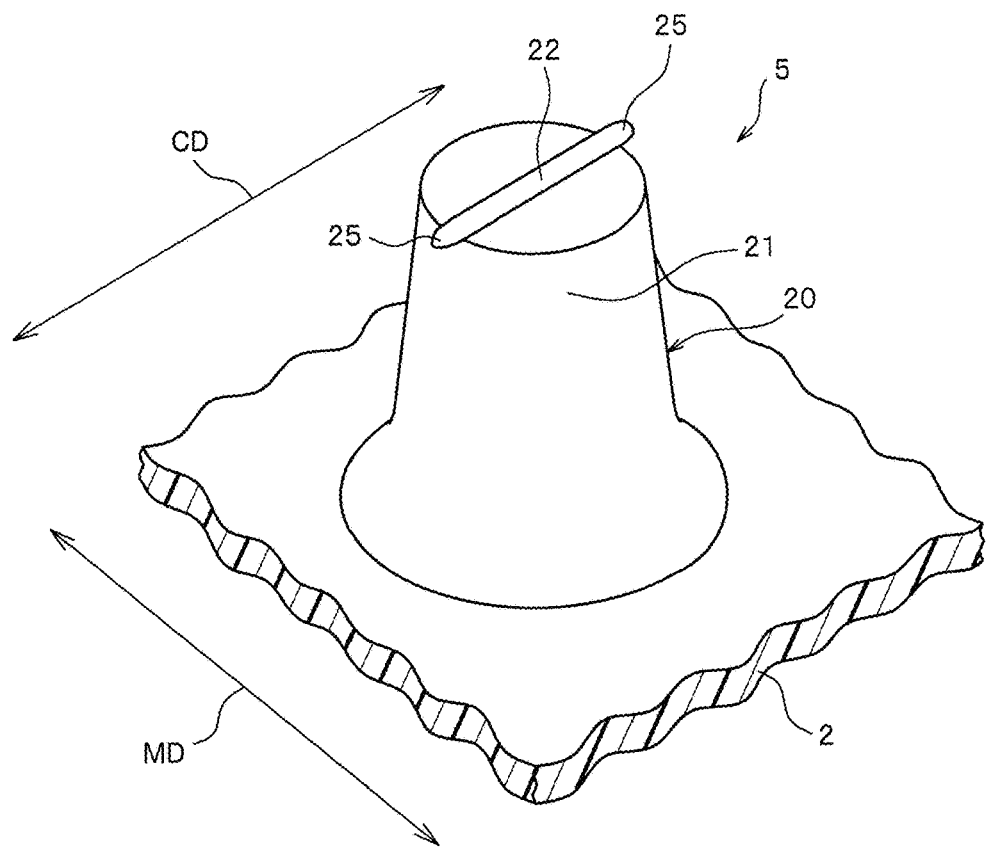
FIG. 15 is a perspective view illustrating a provisional element of the primary molded body.
Figure 16:
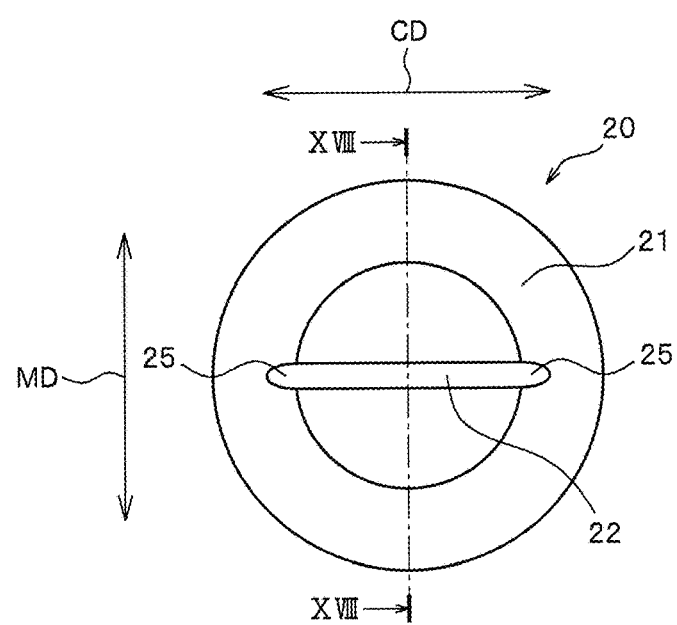
FIG. 16 is a plan view illustrating only the provisional element.
Figure 17:
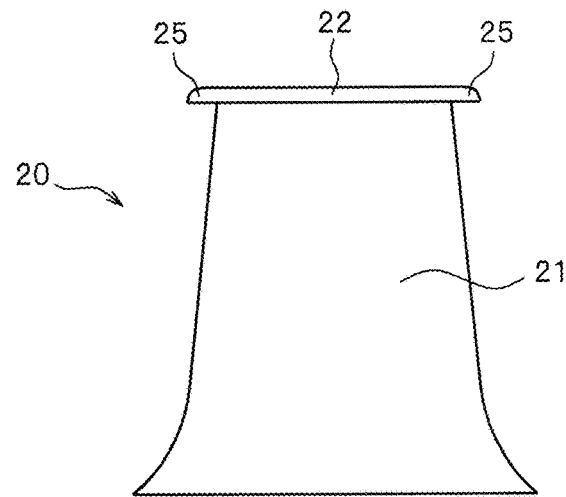
FIG. 17 is a front view viewing only the provisional element from a front and rear direction (MD) of the primary molded body.
Figure 18:
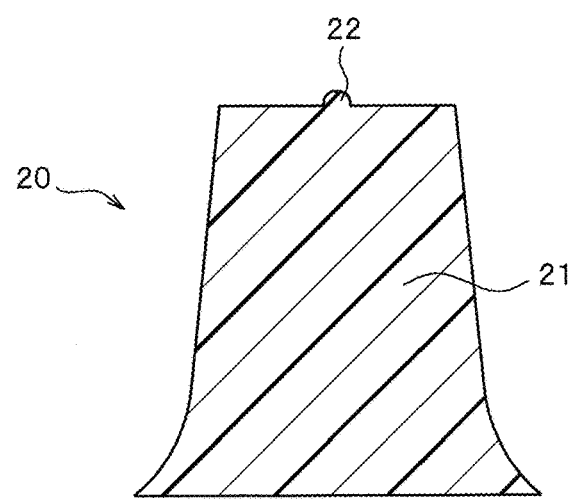
FIG. 18 is a cross-sectional view in XVIII-XVIII line shown in FIG. 16.

As shown in FIGS. 11-13, a plurality of penetration holes 57 penetrating from the outer peripheral surface to the inner peripheral surface of the outer side cylindrical body 52 are provided on the outer side cylindrical body 52 of the die wheel 51 as cavities molding a primary stem portion 21 of the primary molded body 5 as mentioned later. The plurality of penetration holes 57 are formed corresponding to an arrangement of the engaging elements 10 of the molded surface fastener 1 to be manufactured. In a case of Embodiment 1, the plurality of penetration holes 57 are formed in a circumferential direction which is to be an M direction (MD) of the outer side cylindrical body 52 at a predetermined pitch and also formed in a C direction (CD) parallel to a center axis of the outer side cylindrical body 52 at a predetermined pitch.

Such an outer side cylindrical body 52 of Embodiment 1 is formed by manufacturing a cylinder-shaped primary outer side cylindrical body, and then drilling a plurality of penetration holes 57 on the primary outer side cylindrical body at a predetermined position. In this case, the primary outer side cylindrical body is manufactured of metals such as nickel or stainless steel which are conventionally known. It is preferable that the outer side cylindrical body 52 is formed seamless, that is, which has no joint, and can be manufactured by electrocasting or rolling, for example. Further, Known techniques can be used as a processing method of a plurality of penetration holes 57. For example, laser, electron beam, machining, etching or drilling method can be used. It should be noted that, in the present invention, a molding method for the outer side cylindrical body 52, a size of the outer side cylindrical body 52, and a shape and an arrangement of the penetration hole 57 are not limited in particular.

A plurality of concave groove portions 61 are formed on the outer peripheral surface of the inner side cylindrical body 53 of Embodiment 1. The inner side cylindrical body 53 and the concave groove portion 61 can be manufactured also by using the same method as in the case of manufacturing the outer side cylindrical body 52 and the penetration hole 57. Each concave groove portion 61 is concaved linearly along the C direction (CD) parallel to the center axis of the cylinder of the inner side cylindrical body 53, and has a size with which a synthetic resin forming the molded surface fastener 1 can flow into in a molten state. Particularly, in a case of Embodiment 1, the concave groove portion 61 of the inner side cylindrical body 53 is formed in the circumferential direction which is to be an M direction at a predetermined pitch so as to overlap with a diameter of the penetration hole 57 formed on the outer side cylindrical body 52, and crosses with a circular outer peripheral edge of the penetration hole 57 of the outer side cylindrical body 52.

In Embodiment 1, a forming pitch of the penetration hole 57 provided on the outer side cylindrical body 52 in a circumferential direction and a forming pitch of the concave groove portion 61 provided on the inner side cylindrical body 53 in a circumferential direction are set by corresponding each other so as the positions to overlap as above. However, in the present invention, a forming pitch of the penetration hole 57 on the outer side cylindrical body 52 and a forming pitch of the concave groove portion 61 on the inner side cylindrical body 53 do not need to correspond each other. For example, the concave groove portion 61 of the inner side cylindrical body 53 is provided with a forming pitch smaller than the one corresponding to the penetration hole 57 of the outer side cylindrical body, thereby two or more pawl portions 14 can be formed stably on the engaging head portion 12 of each engaging element 10. On the other hand, the concave groove portion 61 of the inner side cylindrical body 53 is provided with a forming pitch larger than the one corresponding to the penetration hole 57 of the outer side cylindrical body 52, thereby the molded surface fastener having both the engaging element 10 in which the pawl portion 14 is protruded on the engaging head portion 12 and the engaging element in which the pawl portion 14 is not protruded on the engaging head portion can be obtained.

Each concave groove portion 61 of the inner side cylindrical body 53 in Embodiment 1 has a groove bottom surface and a pair of groove side wall surfaces disposed opposing and parallel to each other so as a cross section to be a square. In this case, a groove width of each concave groove portion 61 is set to be 0.01 mm or more and 0.10 mm or less, preferably 0.03 mm or more and 0.08 mm or less. A groove depth of each concave groove portion 61 is set to be 0.005 mm or more and 0.05 mm or less, preferably 0.005 or more and 0.03 mm or less, further preferably 0.01 mm or more and 0.025 mm or less.

The groove width of the concave groove portion 61 is set to be 0.01 mm or more and the groove depth is set to be 0.005 mm or more, thereby, in molding the primary molded body 5, the molten synthetic resin can flow from the penetration holes 57 of the outer side cylindrical body 52 into each concave groove portion 61 of the inner side cylindrical body 53 smoothly, and the solidified primary molded body 5 can be demolded from the concave groove portion 61 stably. Further, the groove width of the concave groove portion 61 is set to be 0.10 mm or less and the groove depth is set to be 0.05 mm or less, thereby the above-mentioned micro pawl portion 14 can be stably formed on each engaging element 10 of the molded surface fastener 1. The concave groove portion 61 formed on the inner side cylindrical body 53 may be formed so as to have an approximately U-shaped cross section.

In Embodiment 1, when viewing a position relationship between the penetration hole 57 provided on the outer side cylindrical body 52 and the concave groove portion 61 provided on the inner side cylindrical body 53, a circular-shaped outer peripheral edge of each penetration hole 57 disposed on the inner peripheral surface of the outer side cylindrical body 52 has two groove overlapped parts 58a overlapping with the concave groove portion 61 of the inner side cylindrical body 53 and two arc-shaped close contacting parts 58b disposed between two overlapped parts and directly contacting to the outer peripheral surface of the inner side cylindrical body 53, as shown in FIGS. 12 and 13.

The outer peripheral edge of all the penetration holes 57 has the groove overlapped part 58a and the close contacting part 58b respectively, thereby, when molding the primary molded body 5, a plurality of provisional elements 20 having a primary stem portion 21, a bulging portion 22 and a protruded portion 25 as shown in FIGS. 15-18 can be stably formed on the base portion 2, as mentioned later. Particularly, in this case, the groove width of the concave groove portion 61 is set to be one third, preferably one fifth and further preferably one seventh or less of a dimension in M direction of the penetration hole 57 (in a case of Embodiment 1, a dimension of a diameter of the penetration hole) in the inner peripheral surface of the outer side cylindrical body 52.

The heat press apparatus 70 in the manufacturing apparatus 40 of Embodiment 1 has a pair of upper and lower pressing rollers (calender rollers) 71, 72 disposed on the downstream side of the pickup roller 56, and the upper side pressing roller 71 and the lower side pressing roller 72 are disposed opposing to each other at a predetermined interval. In this case, the interval between the upper side and the lower side pressing rollers 71, 72 can be adjusted by a height adjustment means not shown in Figures, and is adjusted corresponding to a height dimension from a lower surface (back surface) of the base portion 2 to the top end surface of head portion 13a of the engaging head portion 12 in the engaging element 10 of the molded surface fastener 1 to be manufactured.

The upper side pressing roller 71 has a heat source inside not shown in Figures, and a temperature of a surface of the upper side pressing roller 71 is set to be a temperature at which the synthetic resin forming the molded surface fastener 1 can be softened, specifically, a predetermined temperature of −40° C. or more of a melting point of the synthetic resin forming the primary molded body 5 and −10° C. or less of the melting point. The upper side pressing roller 71 is disposed so as to rotate in a counterclockwise direction in FIG. 10, and the outer peripheral surface of the upper side pressing roller 71 becomes a part pressing the heated provisional element 20 of the primary molded body 5 molded in the primary molding step from an upper side.

The lower side pressing roller 72 is disposed so as to rotate in a clockwise direction in FIG. 10, and becomes a supporting surface supporting the primary molded body 5 to be conveyed from a lower side. In the present invention, instead of the upper side pressing roller 71 and/or the lower side pressing roller 72, an upper side belt mechanism and/or a lower side belt mechanism not shown in Figures can be used. In this case, the upper side and lower side belt mechanisms have an endless belt and a pair of left and right rotating rollers which the endless belt is wound around and which rotates the endless belt in one direction.

In a case of manufacturing the molded surface fastener 1 using the manufacturing apparatus 40 having the molding apparatus 50 and the heat press apparatus 70 as above, firstly, a primary molding step for molding the primary molded body 5 by the molding apparatus 50 is conducted. In the primary molding step, the molten synthetic resin material is extruded continuously from the extrusion nozzle 55 toward the peripheral surface of the die wheel 51.

At this time, since the die wheel 51 is rotating drivingly in one direction, the base portion 2 of the molded surface fastener 1 is molded continuously between the extrusion nozzle 55 and the die wheel 51 by extruding the synthetic resin material to the peripheral surface. In this case, an interval between the extrusion nozzle 55 and the die wheel 51 is adjusted so as to correspond to a thickness dimension of the base portion 2 of the molded surface fastener 1 to be manufactured.

At the same time of molding the base portion 2, a plurality of provisional elements 20 as shown in FIGS. 15-18 are integrally molded on the base portion 2 by the above-mentioned outer side and inner side cylindrical bodies 52, 53 of the die wheel 51, thereby the primary molded body 5 is manufactured.

Here, the primary molded body 5 (also referred to as a preliminary molded body) molded by the molding apparatus 50 of Embodiment 1 has a thin plate-shaped base portion 2 and a plurality of provisional elements 20 standing on an upper surface of the base portion 2, as shown in FIGS. 15-18. The base portion 2 of the primary molded body 5 becomes the base portion 2 of the molded surface fastener 1 as it is.

The provisional element 20 formed on the primary molded body 5 is a part which becomes an engaging element 10 of the molded surface fastener 1 by being pressed and molded in a secondary molding step. In this case, each provisional element 20 has a frustum of cone-shaped primary stem portion 21 standing on the base portion 2, a stick-shaped bulging portion 22 bulging partially from an upper surface of the primary stem portion 21 upward, and two protruded portions (provisional pawl portions) 25 formed integrally and continuously to the bulging portion 22 and protruding so as to bulge to an outside of the primary stem portion 21.

The primary stem portion 21 is molded by the synthetic resin being filled into the penetration holes 57 provided on the outer side cylindrical body 52, and has a frustum of cone shape such that a cross section orthogonal to the upper and lower direction gradually increases as close to the base portion 2.

The primary stem portion 21 becomes a stem portion 11 of the molded surface fastener 1 by pressing the provisional element 20 from the upper side in the secondary molding step and deforming an upper end part of the primary stem portion 21. Therefore, a lower end part of the primary stem portion 21 has the same shape as the lower end part of the stem portion 11. The primary stem portion 21 can be formed to be a truncated pyramid shape such as a truncated square pyramid, a columnar shape, or a prism shape such as a quadrangular prism corresponding to the shape of the stem portion 11 of the molded surface fastener 1 to be manufactured.

The bulging portion 22 and the protruded portion (provisional pawl portion) 25 are molded such that the synthetic resin flows from the penetration holes 57 of the outer side cylindrical body 52 into the concave groove portions 61 provided on the inner side cylindrical body 53 and enters along the concave groove portions 61 and into a part beyond the penetration holes 57 in the primary molding step. In this case, the bulging portion 22 is formed on the upper surface of the primary stem portion 21 along the C direction (CD), and two protruded portions 25 are formed protruding from both end parts of the bulging portion 22 in the C direction orthogonal to an erecting direction of the primary stem portion 21 beyond the primary stem portion 21.

The bulging portion 22 and the protruded portion 25 are molded by the concave groove portion 61 whose cross section provided on the inner side cylindrical body 53 is square-shaped. However, due to a shrinking in cooling and solidifying the bulging portion 22 and the protruded portion 25, they have a stick shape whose cross section appears an approximately U-shape with roundness.

The molding of the protruded portion 25 is conducted not by filling the synthetic resin into all concave portions 61 of the inner side cylindrical body 53, but the protruded portion 25 is formed such that the synthetic resin flowing from the penetration holes 57 of the outer side cylindrical body 52 into the concave groove portions 61 enters into a part of the concave groove portions 61 along the concave groove portion 61 so as to overflow a forming region of the penetration hole 57 a little (for example, a distance of about 0.01 mm or more and 0.04 or less from a region of the penetration hole 57). The protruded portion 25 molded in the primary molding step is a part which becomes the pawl portion 14 of the molded surface fastener 1 by pressing the provisional element 20 from the upper side in the secondary molding step.

The primary molded body 5 molded in the primary molding step can be obtained such that the molten synthetic resin extruded from the extrusion nozzle 55 is solidified by being held on the outer peripheral surface of the die wheel 51, cooled and half rotated. Thereafter, the primary molded body 5 is peeled off continuously from the outer peripheral surface of the die wheel 51 by the pickup roller 56. At this time, the protruded portion 25 of the primary molded body 5 is pulled out smoothly from the concave groove portion 61 of the inner side cylindrical body 53 and the penetration hole 57 of the outer side cylindrical body 52 while elastic deforming.

The primary molded body 5 peeled off from the die wheel 51 is conveyed toward the heat press apparatus 70 which conducts the secondary molding step, and introduced between the upper side pressing roller 71 and the lower side pressing roller 72 of the heat press apparatus 70.

In the secondary molding step, when the primary molded body 5 passes between the upper side and the lower side pressing rollers 71, 72, at least upper end part of each provisional element 20 of the primary molded body 5 is softened by heating of the upper side pressing roller 71, while the base portion 2 of the primary molded body 5 is held by the lower side pressing roller 72 from the lower side, each provisional element 20 of the primary molded body 5 is pressed by the upper side pressing roller 71 from the upper side thereby the upper end part of the provisional element 20 is compressed. At this time, a temperature of the peripheral surface of the roller in the upper side pressing roller 71 is set to be a predetermined temperature of −40° C. or more of a melting point of the synthetic resin of the primary molded body and −10° C. or less of the melting point, as described above.

Due to the above, the engaging head portion 12 having the top end surface of head portion 13a which was made flat by the outer peripheral surface of the upper side pressing roller 71 after the upper end part of the primary stem portion 21, the bulging portion 22 and the protruded portion 25 in the provisional element 20 are thermal deformed is molded, and the pawl portion 14 protruding from the outer peripheral side surface 13c of the engaging head portion 12 is molded by the protruded portion 25. Thus, the molded surface fastener 1 of Embodiment 1 shown in FIG. 1 is manufactured.

Thereafter, the manufactured molded surface fastener 1 which is long in a machine direction is conveyed to a cutting part not shown in Figures, then cut in a predetermined length at the cutting part and collected, or is wound as a roll shape by a collecting roller in a state of long molded surface fastener 1 and collected.

In the molded surface fastener 1 of Embodiment 1 manufactured as above, two micro pawl portions 14 protruding along the C direction are provided on the engaging head portion 12 of each engaging element 10 respectively. Particularly, each pawl portion 14 in Embodiment 1 has a concave surface-shaped back surface of pawl 15b curving to a lower side than the back surface of head portion 13b of the engaging head portion 12. Therefore, when the molded surface fastener 1 of Embodiment 1 is engaged with a loop which becomes an engaging element 10 of a female surface fastener, the loop of the female surface fastener easily hook with the pawl portion 14 of each engaging element 10 and the loop is hard to slip off from each engaging element 10.

Accordingly, the molded surface fastener 1 of Embodiment 1 has a more substantial engaging strength (peeling strength) than conventional and ordinary molded surface fasteners not having the pawl portion 14, and an engaging state with respect to the female surface fastener can be stably maintained.

Moreover, in the molded surface fastener 1 of Embodiment 1, the top end surface of head portion 13a and the outer peripheral side surface of head portion 13c of the engaging head portion 12 of each engaging element 10 are formed as smooth and continuous surface. In addition, the pawl portion 14 provided so as to enhance the engaging strength is formed to be smaller than the engaging head portion 12, and the upper surface of the pawl portion 14 is formed as a curved surface declining toward the pawl tip end.

Therefore, an effect which the pawl portion 14 gives on tactile of the molded surface fastener 1 can be limited. As a result, the molded surface fastener 1 of Embodiment 1 can have a comfortable texture such as smooth tactile or soft and flexible tactile can be obtained when the molded surface fastener 1 is touched from the upper surface side in which the engaging elements 10 are standing.

The molded surface fastener 1 of Embodiment 1 which has a substantial engaging strength and a comfortable texture as above is preferably used for goods to be put on and taken off from the body, for example, such as a disposable diaper, a diaper cover for babies, a supporter protecting joints of arms and legs, a corset for waist and gloves.

Embodiment 2

Figure 19:
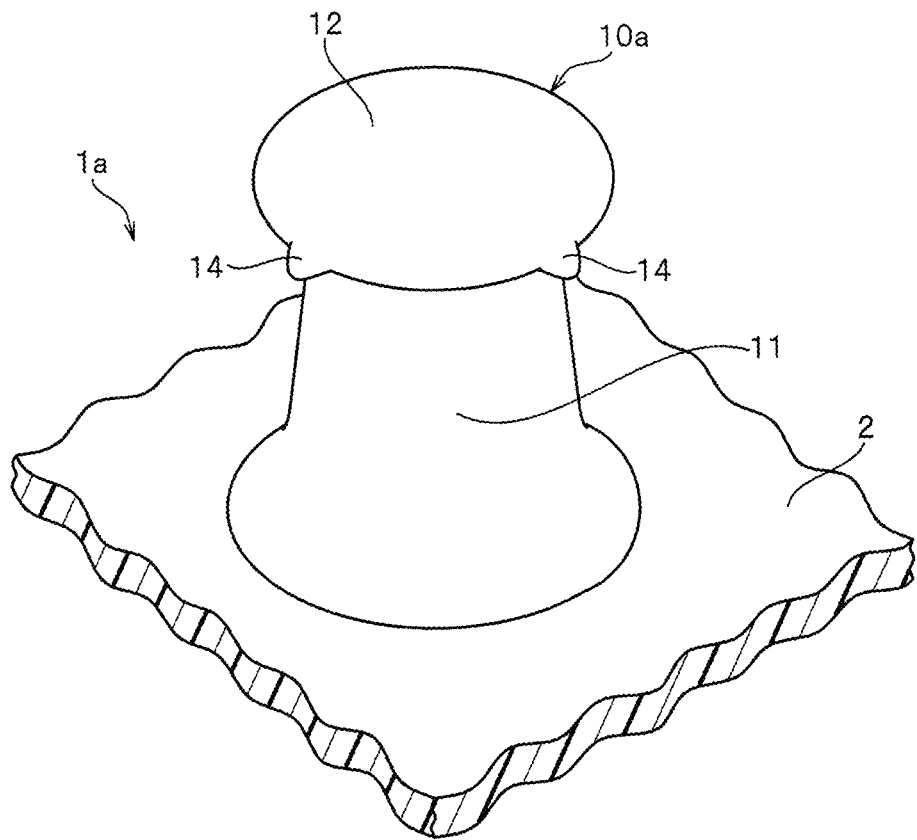
FIG. 19 is a perspective view illustrating an engaging element of a molded surface fastener according to Embodiment 2 of the invention.
Figure 20:
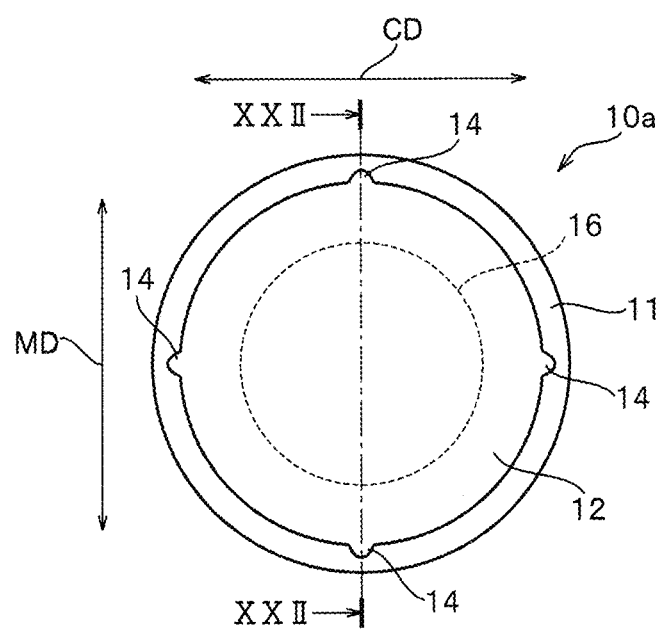
FIG. 20 is a plan view illustrating only the engaging element.
Figure 21:
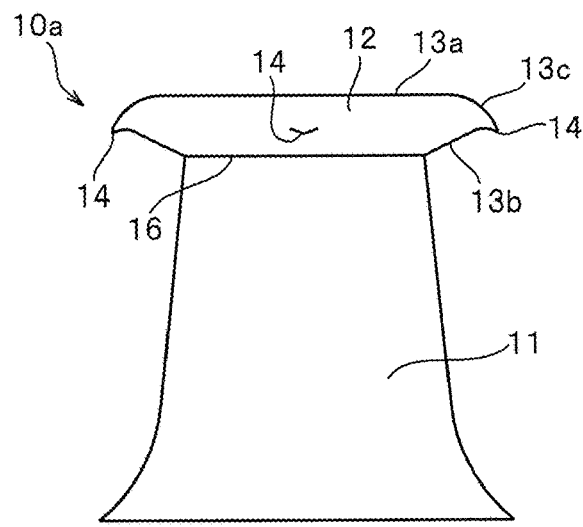
FIG. 21 is a front view viewing only the engaging element from a front and rear direction (MD) of the molded surface fastener.
Figure 22:
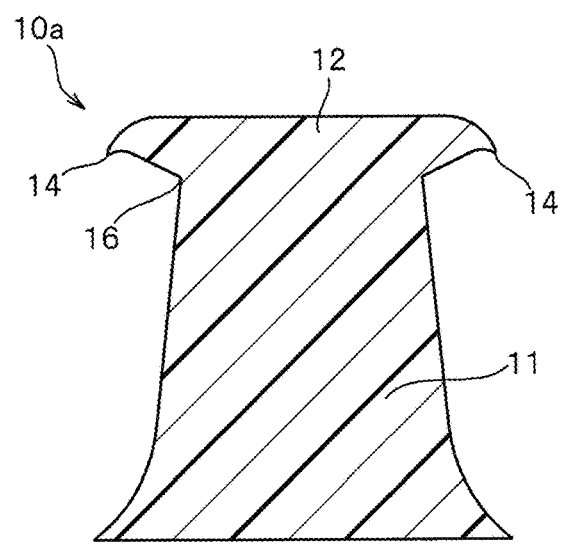
FIG. 22 is a cross-sectional view in XXII-XXII line shown in FIG. 20.

FIGS. 19-21 are views viewing an engaging element provided in the molded surface fastener of Embodiment 2 from various directions, and FIG. 22 is a cross-sectional view of the engaging element.

It should be noted that, the molded surface fastener 1a of Embodiment 2 is formed so as the number of the pawl portion 14 provided on the engaging head portion 12 of each engaging element 10a to be four, which is different from the above mentioned Embodiment 1, but is substantially the same as the molded surface fastener 1 explained in the above-mentioned Embodiment 1 except that the number of disposition of the pawl portion 14 is changed.

Accordingly, in Embodiment 2, and Embodiment 3 and each modification example described later, different structures from the molded surface fastener 1 according to the above-mentioned Embodiment 1 are mainly explained. The explanation of parts or members having substantially the same structures as the molded surface fastener 1 according to the above-mentioned Embodiment 1 is omitted by using the same reference signs.

The molded surface fastener 1a of Embodiment 2 has a thin plate-shaped base portion 2 and a plurality of engaging elements 10a erected vertically from an upper surface of the base portion 2, and a plurality of engaging elements 10a are disposed lining along the M direction (MD) and the C direction (CD). Each engaging element 10a has a stem portion 11 standing on the base portion 2, a disc-shaped engaging head portion 12 formed integrally on the stem portion 11 and four pawl portions 14 protruded in the outer peripheral edge part of the engaging head portion 12.

In the engaging element 10a of Embodiment 2, four pawl portions 14 are protruded from the outer peripheral side surface 13c of the engaging head portion 12 and from the engaging head portion 12 in the M direction and the C direction along a radial direction of the engaging head portion 12. The four pawl portions 14 are arranged regularly at positions of 0°, 90°, 180°, 270° about a center of the engaging head portion 12 appearing a circular shape in a plan view of the engaging element 10a shown in FIG. 20.

A shape and a size of respective pawl portions 14 in Embodiment 2 are the same as each pawl portion 14 provided in the molded surface fastener 1 of the above-mentioned Embodiment 1. Each pawl portion 14 has a curved surface-shaped upper surface of pawl 15a declining toward a tip end, a back surface of pawl 15b curving concavely and disposed opposing to the base portion 2 and a pair of side wall surfaces 15c disposed between the upper surface of pawl 15a and the back surface of pawl 15b.

The molded surface fastener 1a of Embodiment 2 having the engaging elements 10a in which four pawl portions 14 as above are disposed is manufactured by using the manufacturing apparatus 40 having the molding apparatus 50 and the heat press apparatus 70 as shown in FIG. 10, as in the case of the above-mentioned Embodiment 1.

It should be noted that, in a case of Embodiment 2, a cylinder-shaped inner side cylindrical body 53a forming the die wheel 51 of the molding apparatus 50 has a different structure from the inner side cylindrical body 53 used in the above-mentioned Embodiment 1 to provide four pawl portions 14 on each engaging element 10a.

The inner side cylindrical body (inner side sleeve) 53a used in Embodiment 2 has a plurality of concave groove portions 62 formed on the outer peripheral surface. However, on the outer peripheral surface of the inner side cylindrical body 53a, not only linear-shaped concave groove portions 62 along the C direction as in the above-mentioned Embodiment 1 but also a plurality of concave groove portions 62 along a circumferential direction of the cylinder which is to be the M direction are concaved.

That is, the concave groove portion 62 of Embodiment 2 has a plurality of first concave groove portions 62a along the C direction and a plurality of second concave groove portions 62b along the circumferential direction of the cylinder which is to be the M direction. In this case, the first concave groove portion 62a disposed along the C direction of the inner side cylindrical body 53a and the second concave groove portion 62b disposed along the M direction overlap respectively with the diameter of the penetration hole 57 formed on the outer side cylindrical body 52 and are formed at a predetermined pitch respectively so as the first and the second concave groove portions 62a, 62b to cross orthogonally to each other at a center position of each penetration hole 57.

The circular-shaped outer peripheral edge of each penetration hole 57 disposed on the inner peripheral surface of the outer side cylindrical body 52 has four groove overlapped parts 58a overlapping with the first and the second concave groove portions 62a, 62b of the inner side cylindrical body 53a and four arc-shaped close contacting parts 58b directly contacting with the outer peripheral surface of the inner side cylindrical body 53a.

Figure 24:
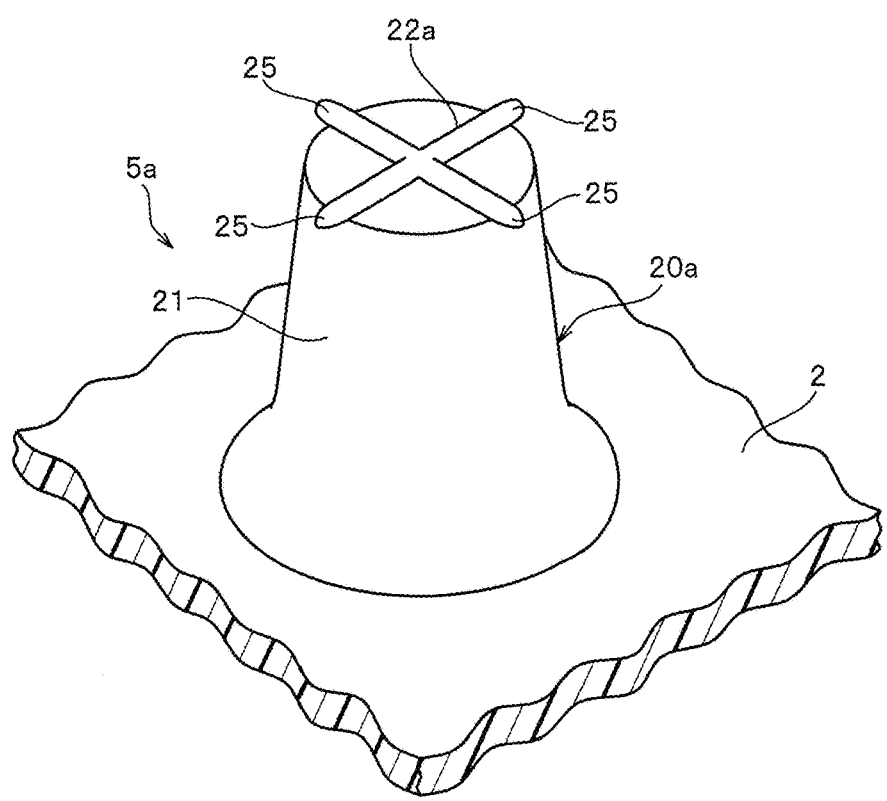
FIG. 24 is a perspective view illustrating a provisional element of a primary molded body according to Embodiment 2 of the invention.
Figure 25:
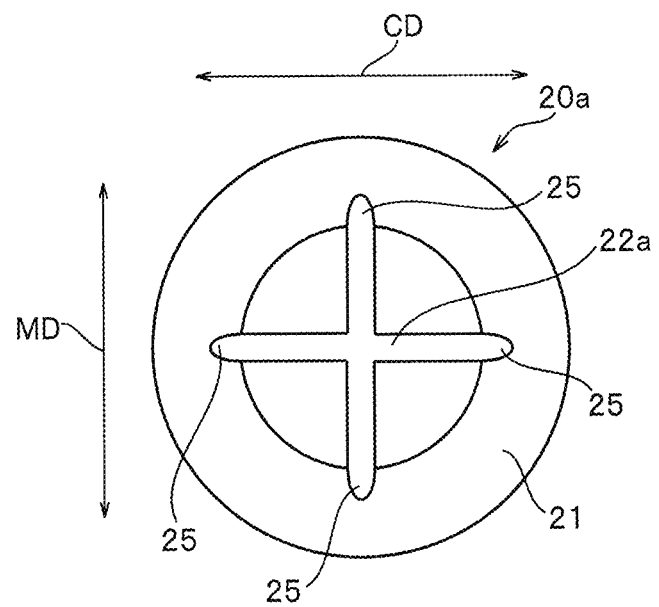
FIG. 25 is a plan view illustrating only the provisional element.
Figure 26:
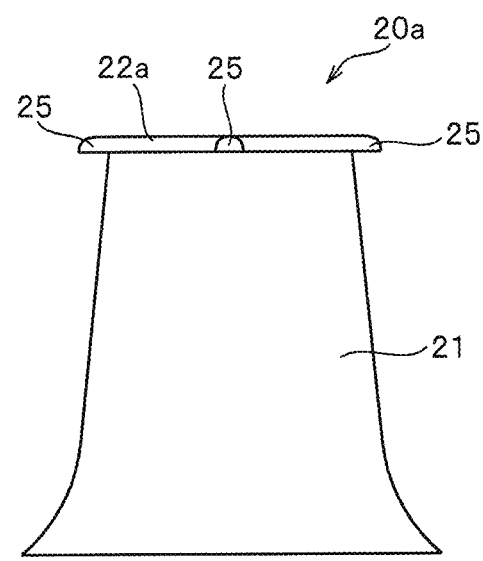
FIG. 26 is a front view viewing only the provisional element from a front and rear direction (MD) of the primary molded body.

In Embodiment 2, by conducting the primary molding step using the molding apparatus 50 having the above-mentioned inner side cylindrical body 53a, a primary molded body 5a having a plurality of provisional elements 20a as shown in FIGS. 24-26 on the base portion 2 is molded. In this case, each provisional element 20a has a frustum of cone-shaped primary stem portion 21 standing on the base portion 2, a bulging portion 22a bulging partially from the upper surface of the primary stem portion 21 upward and crossing as a + figure shape and four protruded portions 25 extending so as to bulge from the bulging portion 22a to an outside of the primary stem portion 21.

In this case, the bulging portion 22a and the protruded portion 25 are molded such that the synthetic resin flows from the penetration hole 57 of the outer side cylindrical body 52 into the first and the second concave groove portions 62a, 62b provided on the inner side cylindrical body 53a in the primary molding step. The bulging portion 22a is formed on the upper surface of the primary stem portion 21 along the C direction and the M direction, and four protruded portions 25 are protruding continuously from each end part of the + figure-shaped bulging portion 22a in the C direction and the M direction. Therefore, the bulging portion 22a and the protruded portion 25 in Embodiment 2 appears as + figure-shaped in which two stick-shaped bodies are orthogonal to each other in a plan view of the provisional element 20a.

Thereafter, the primary molded body 5a having the provisional element 20a shown in FIGS. 24-26 is conveyed to the heat press apparatus 70 by which the secondary molding step is conducted, and as in the case of the above-mentioned Embodiment 1, each provisional element 20a is heated and pressed from the upper side. Thus, the molded surface fastener 1a of Embodiment 2 is manufactured. In this case, four protruded portions 25 provided on each provisional element 20a of the primary molded body 5a becomes four pawl portions 14 disposed on each engaging element 10 of the molded surface fastener 1a by the secondary molding step.

In the molded surface fastener 1a of Embodiment 2 manufactured as above, the number of the pawl portion 14 provided on each engaging element 10a is four, which is more than in the case of the above-mentioned Embodiment 1. Therefore, the stronger engaging force than the molded surface fastener 1a of Embodiment 1 can be easily obtained. In addition, since a size and a shape of each pawl portion 14 itself is the same as in the case of the above-mentioned Embodiment 1, a texture of the surface (upper surface) of the molded surface fastener 1a can be comfortable.

Embodiment 3

Figure 27:
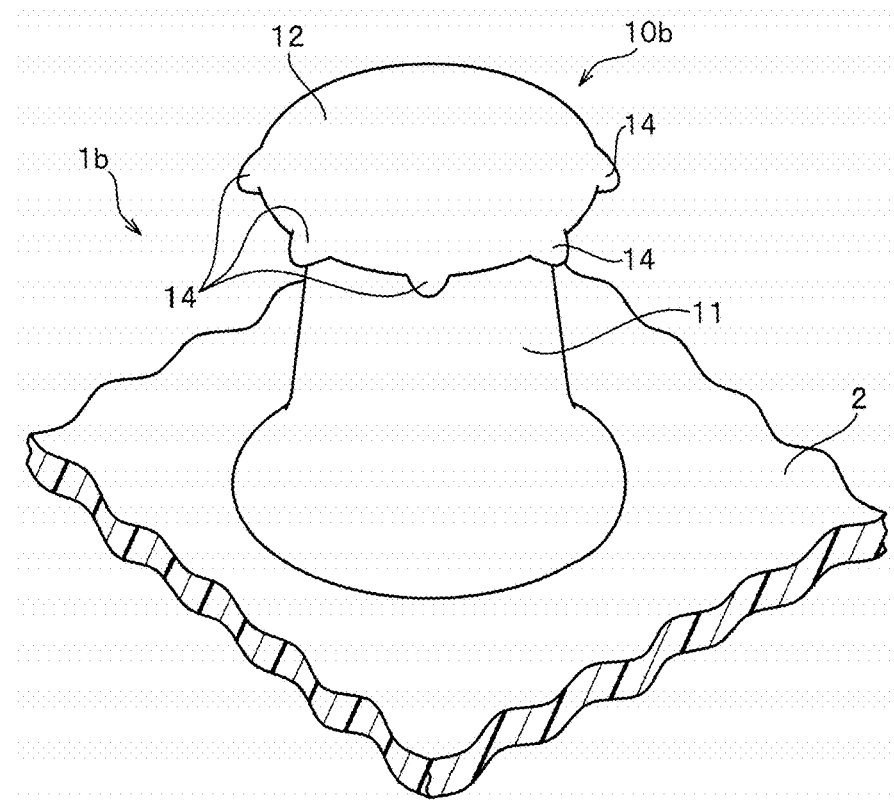
FIG. 27 is a perspective view illustrating an engaging element of a molded surface fastener according to Embodiment 3 of the invention.
Figure 28:
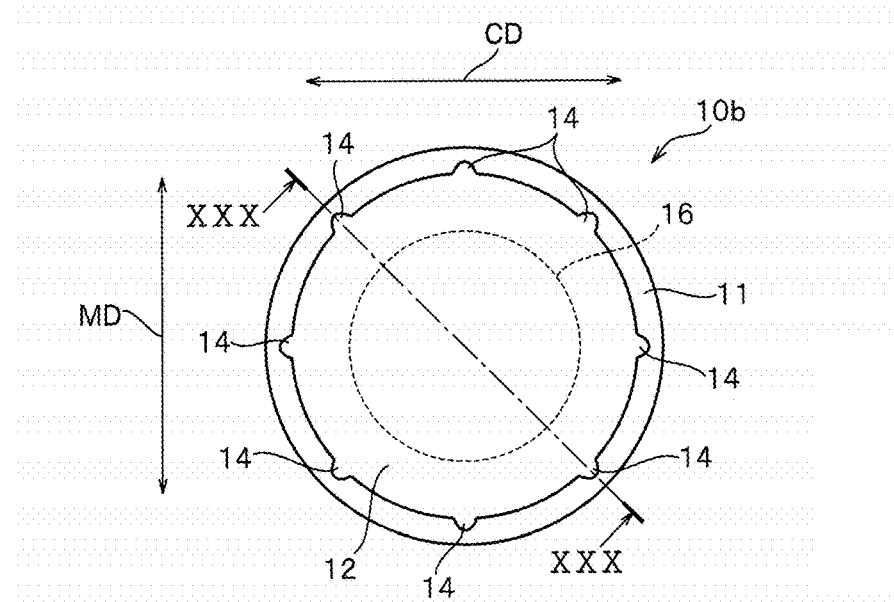
FIG. 28 is a plan view illustrating only the engaging element.
Figure 29:
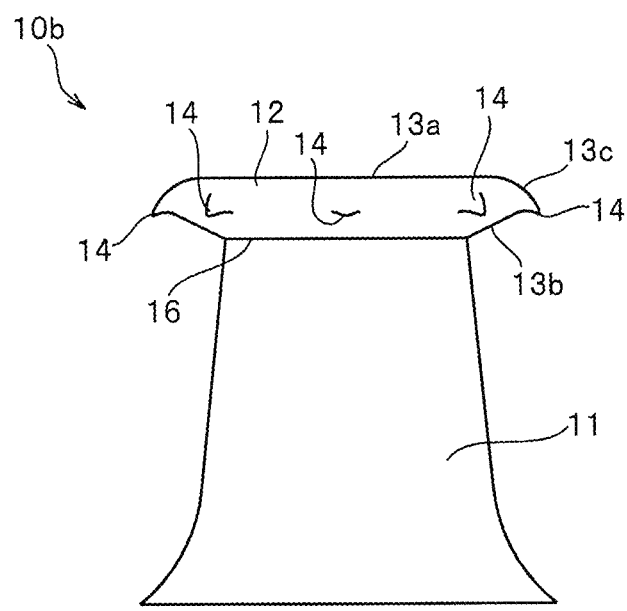
FIG. 29 is a front view viewing only the engaging element from a front and rear direction (MD) of the molded surface fastener.
Figure 30:
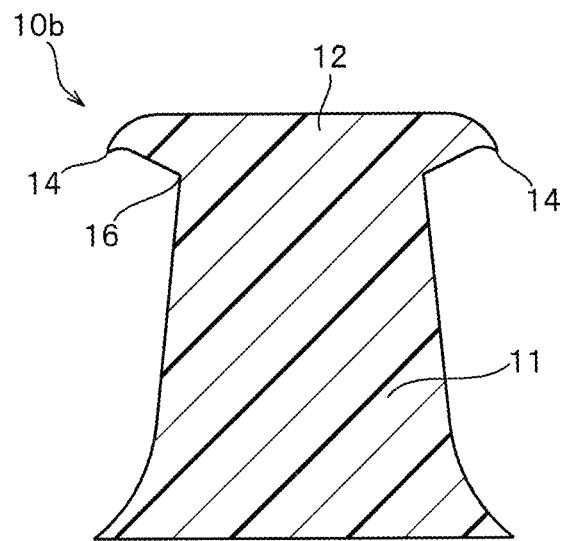
FIG. 30 is a cross-sectional view in XXX-XXX line shown in FIG. 28.

FIGS. 27-29 are views viewing the engaging element provided in the molded surface fastener of Embodiment 3 from various directions, and FIG. 30 is a cross section of the engaging element.

The molded surface fastener 1b of Embodiment 3 has a thin plate-shaped base portion 2 and a plurality of engaging elements 10b erected vertically from the upper surface of the base portion 2. Each engaging element 10b has a stem portion 11 standing on the base portion 2, a disc-shaped engaging head portion 12 formed integrally on the stem portion 11 and eight pawl portions 14 protruding on the outer peripheral edge part of the engaging head portion 12. A shape and a size of each pawl portion 14 in Embodiment 3 are the same as each pawl portion 14 formed in the molded surface fastener 1 of the above-mentioned Embodiment 1.

In the engaging element 10b of Embodiment 3, eight pawl portions 14 are protruded from the outer peripheral side surface 13c of the engaging head portion 12 toward an outside along a radial direction of the engaging head portion 12. The eight pawl portions 14 are arranged regularly at a predetermined interval so as to have an angle of 45° with respect to the adjacent pawl portions 14 about a center of the engaging head portion 12 appearing a circular shape in a plan view of the engaging element 10b shown in FIG. 28.

The molded surface fastener 1b of Embodiment 3 having such an engaging element 10b is, as in the case of the above-mentioned Embodiment 1, manufactured by using the manufacturing apparatus 40 having the molding apparatus 50 and the heat press apparatus 70 as shown in FIG. 10.

In a case of Embodiment 3, the cylinder-shaped inner side cylindrical body (inner side sleeve) 53b forming the die wheel 51 of the molding apparatus 50 is different from the inner side cylindrical body 53 used in the above-mentioned Embodiment 1 to provide eight pawl portions 14 on each engaging element 10b. That is, on the outer peripheral surface of the inner side cylindrical body 53b of Embodiment 3, a plurality of linear-shaped first concave groove portions 63a disposed along the C direction, a plurality of second concave groove portions 63b disposed along the circumferential direction of the cylinder which is to be the M direction and a plurality of third and fourth concave groove portions 63c, 63d disposed at an inclination angle of 45° with respect to the first and the second concave groove portions 63a, 63b are concaved.

In this case, the first concave groove portion 63a—the fourth concave groove portion 63d overlaps with a diameter of the penetration holes 57 formed on the outer side cylindrical body 52 and are formed at a predetermined pitch respectively so as to cross each other at a center position of each penetration hole 57. The circular-shaped outer peripheral edge of each penetration hole 57 disposed on the inner peripheral surface of the outer side cylindrical body 52 has groove overlapped parts 58*a* overlapping with the first concave grove portion 63*a*—the fourth concave groove portion 63*d* of the inner side cylindrical body 53*b* and arc-shaped close contacting parts 58*b* directly contacting with the outer peripheral surface of the inner side cylindrical body 53*b*.

Figure 32:
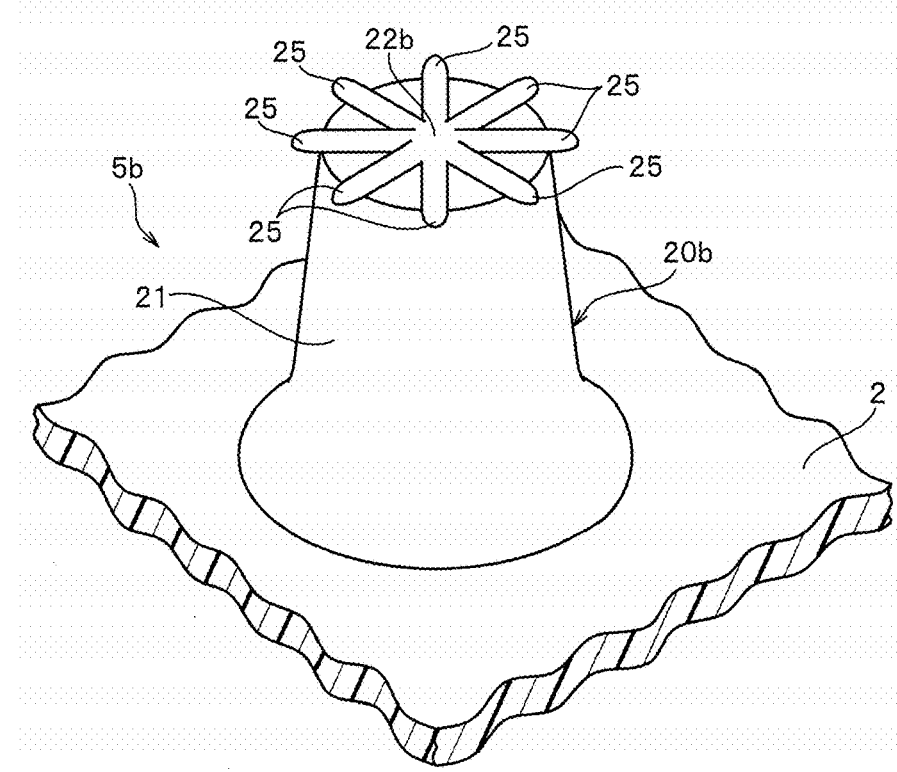
FIG. 32 is a perspective view illustrating a provisional element of the primary molded body according to Embodiment 3 of the invention.
Figure 33:
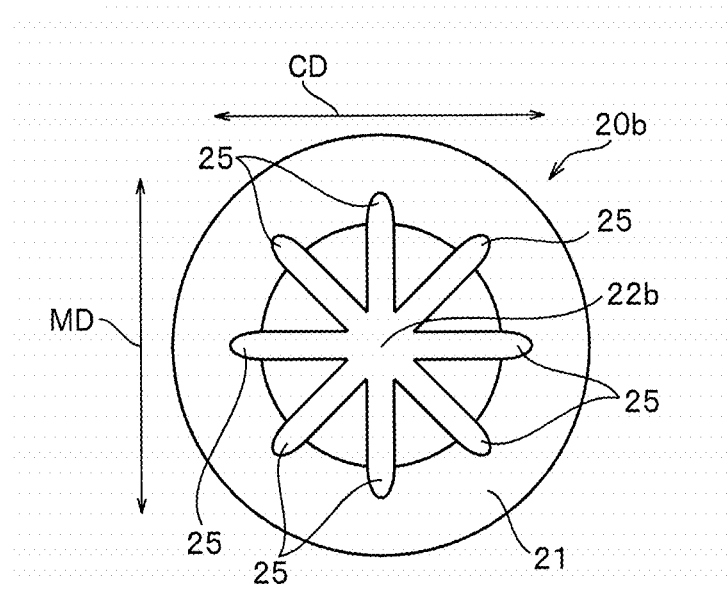
FIG. 33 is a plan view illustrating only the provisional element.

In Embodiment 3, by conducting the primary molding step by using the molding apparatus 50 having the above-mentioned inner side cylindrical body 53*b*, a primary molded body 5*b* having a plurality of provisional elements 20*b* as shown in FIGS. 32 and 33 on the base portion 2 is formed. In this case, each provisional element 20*b* has a frustum of cone-shaped primary stem portion standing on the base portion 2, a bulging portion 22*b* bulging from the upper surface of the primary stem portion 21 upward and crossing as + figure-shaped as well as × figure-shaped and eight protruded portions 25 extending so as to bulge from each end part of the bulging portion 22*b* to an outside of the primary stem portion 21.

In this case, the bulging portion 22*b* and the protruded portion 25 are molded such that the synthetic resin flows from the penetration holes 57 of the outer side cylindrical body 52 into the first concave groove portions 63*a*—the fourth concave groove portions 63*d* provided on the inner side cylindrical body 53*b* in the primary molding step. The bulging portion 22*b* is formed on the upper surface of the primary stem portion 21 along the C direction, the M direction and a direction crossing with the C and M directions at an inclination angle of 45°, and eight protruded portions 25 are formed protruding from each end part of the bulging portion 22*b* in a radial direction. Therefore, the bulging portion 22*b* and the protruded portion 25 of Embodiment 3 appear a shape in which four stick-shaped bodies are crossing each other with an angle of 45° and + figure and × figure are combined in a plan view of the provisional element 20*b*.

Thereafter, the primary molded body 5*b* having a provisional element 20*b* shown in FIGS. 32 and 33 are conveyed to the heat press apparatus 70 and the secondary molding step is conducted, thereby the molded surface fastener 1*b* of Embodiment 3 is manufactured.

In the molded surface fastener 1*b* of Embodiment 3 manufactured as above, the number of the pawl portion 14 provided on each engaging element 10*b* is eight, which is more than in the case of the above-mentioned Embodiment 1. Therefore, stronger engaging force can be easily obtained. Moreover, since a size and a shape of each pawl portion 14 itself are the same as in the case of the above-mentioned Embodiment 1, a texture of the surface (upper surface) of the molded surface fastener 1*b* can be comfortable.

It should be noted that, in the present invention, the number, a shape, a size and an arrangement of the pawl portion provided on each engaging element of the molded surface fastener are not limited to the above-mentioned Embodiment 1-Embodiment 3, and can be changed arbitrarily according to a usage of the molded surface fastener.

For example, in the present invention, in the die wheel 51 of the molding apparatus 5 conducting the primary molding step as described above, forming pitches of the concave groove portions 61, 62, 63*a*-63*d* provided on the cylinder-shaped inner side cylindrical bodies 53, 53*a*, 53*b* can be arbitrarily changed so as not to correspond intentionally to forming pitches of the penetration hole 57 provided on the cylinder-shaped outer side cylindrical body in a circumferential direction or an axis direction.

For example, the forming pitches of the concave groove portions 61, 62, 63*a*-63*d* of the inner side cylindrical bodies 53, 53*a*, 53*b* are set to be smaller than the forming pitches of the penetration hole 57 of the outer side cylindrical body 52, thereby the number of the pawl portion provided on the engaging head portion can be different among each engaging element. On the other hand, the forming pitches of the concave groove portions 61, 62, 63*a*-63*d* of the inner side cylindrical bodies 53, 53*a*, 53*b* can be set to be wider than the forming pitches of the penetration hole 57 of the outer side cylindrical body 52. Thereby, not only the number of the pawl portion provided on the engaging head portion can be different among each engaging element, but also the molded surface fastener in which the engaging elements in which the pawl portion is provided on the engaging head portion and the engaging element in which the pawl portion is not provided on the engaging head portion are standing can be obtained.

In the aforementioned Embodiment 1-Embodiment 3, a plurality of concave groove portions 61, 62, 63*a*-63*d* are formed on one inner side cylindrical body 53, 53*a*, 53*b* with the same groove width and the groove depth. However, in the present invention, it is possible that a plurality of concave groove portions 61, 62, 63*a*-63*d* having different groove width or the different groove depth are provided on one inner side cylindrical body 53, 53*a*, 53*b*. Thereby, a protruding angle and a size of the pawl portion provided on the engaging head portion can be different from each other among each engaging element. Further, for example, in a case that a plurality of pawl portions are provided with respect to one engaging head portion, it is also possible that a plurality of pawl portions protruding at different angles or a plurality of pawl portions having different sizes are provided with respect to the one engaging head portion.

In the present invention, a configuration of the pawl portion can be arbitrarily and easily changed by changing the forming pattern of the concave groove portion or the concave portion provided on the inner side cylindrical body of the molding apparatus which conducts the primary molding step. Here, the forming pattern of the concave groove portion or the concave portion provided on the inner side cylindrical body is explained showing some modification examples and using Figures. FIGS. 34-41 are main part schematic views explaining schematically a position relationship between the concave groove portion or the concave portion provided on the inner side cylindrical body and the penetration hole provided on the outer side cylindrical body in each modification example.

In these Figures, two circles express the outer peripheral edge of the penetration hole disposed on the inner peripheral surface of the outer side cylindrical body. A white part expresses the concave groove portion or the concave portion provided on the outer peripheral surface of the inner side cylindrical body, and a gray part expresses a part of the outer peripheral surface of the cylinder on which the concave groove portion or the concave portion of the inner side cylindrical body is not provided.

Figure 34:
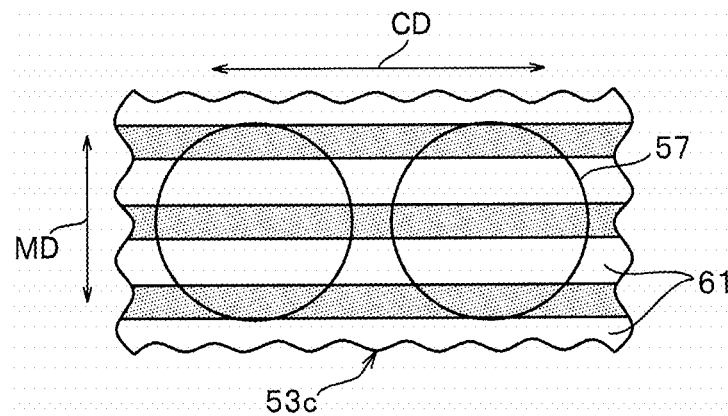
FIG. 34 is a main part schematic view illustrating a position relationship between penetration holes of an outer side cylindrical body and concave groove portions of an inner side cylindrical body according to modification example 1.

In modification example 1 shown in FIG. 34, a plurality of concave groove portions 61 disposed linearly along the C direction (CD) are concaved on the outer peripheral surface of the inner side cylindrical body (inner side sleeve) 53*c* so as to form a stripe pattern. For example, in the aforementioned Embodiment 1, only one concave groove portion 61 disposed on the inner side cylindrical body 53 in the C direction is, as shown in FIG. 12, formed at a position along the diameter of the penetration hole 57 with respect to one circular penetration hole 57 of the outer side cylindrical body 52. However, in the modification example 1, by making the interval (forming pitch) between each concave groove portion 61 smaller than the above-mentioned Embodiment 1, a plurality of concave groove portions 61 are arranged so as to cross over one circular penetration hole 57 of the outer side cylindrical body 52.

In this case, by changing the size of the penetration hole 57 formed on the outer side cylindrical body 52 or the groove width dimension and the forming interval of the concave groove portion 61 formed on the inner side cylindrical body 53*c* appropriately, the number of the concave groove portion 61 in the C direction formed with respect to one circular penetration hole 57 can be easily changed.

As the modification example 1, the molded surface fastener is manufactured by using the inner side cylindrical body 53*c* on which multiple concave groove portions 61 in the C direction are formed with respect to one circular penetration hole 57 of the outer side cylindrical body 52, thereby the molded surface fastener having the engaging element in which three or more pawl portions are protruded regularly or irregularly on the outer peripheral edge part of the engaging head portion can be easily obtained.

In the above-mentioned Embodiment 1 and the modification example 1, the concave groove portions 61 in the C direction having a constant groove width dimension are provided on the outer peripheral surfaces of the inner side cylindrical bodies 53, 53*c* at a constant forming pitch so as the number to be one or plural with respect to one circular penetration hole 57 of the outer side cylindrical body 52. However, in the present invention, it is also possible that a plurality of concave groove portions with different groove width dimensions or with different forming pitches are provided on the outer peripheral surface of the inner side cylindrical bodies 53, 53*c*.

Figure 35:
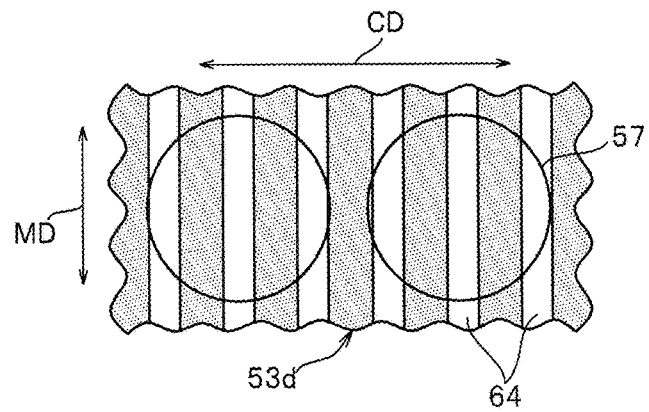
FIG. 35 is a main part schematic view illustrating a position relationship between penetration holes of an outer side cylindrical body and concave groove portions of an inner side cylindrical body according to modification example 2.
Figure 36:
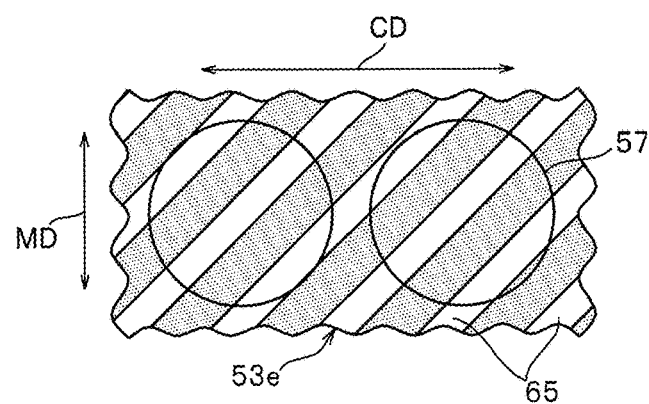
FIG. 36 is a main part schematic view illustrating a position relationship between penetration holes of an outer side cylindrical body and concave groove portions of an inner side cylindrical body according to modification example 3.

Further, in the present invention, it is also possible that the molded surface fastener is manufactured not by forming the concave groove portion in the C direction on the outer peripheral surface of the inner side cylindrical body, but by providing only a plurality of concave groove portions 64 along the circumferential direction of the cylinder which is to be the M direction on the inner side cylindrical body 53*d* as the modification example 2 is shown in FIG. 35, or by providing only a plurality of concave groove portions 65 inclining with a predetermined angle with respect to the C direction or the M direction on the inner side cylindrical body 53*e* as the modification example 3 are shown in FIG. 36.

Figure 23:
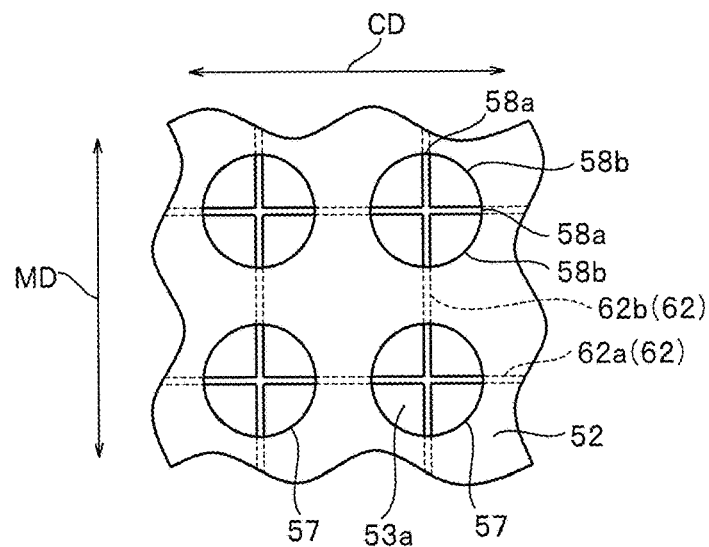
FIG. 23 is a main part schematic view illustrating a position relationship between penetration holes formed on an outer side cylindrical body and concave groove portions provided on an inner side cylindrical body.
Figure 31:
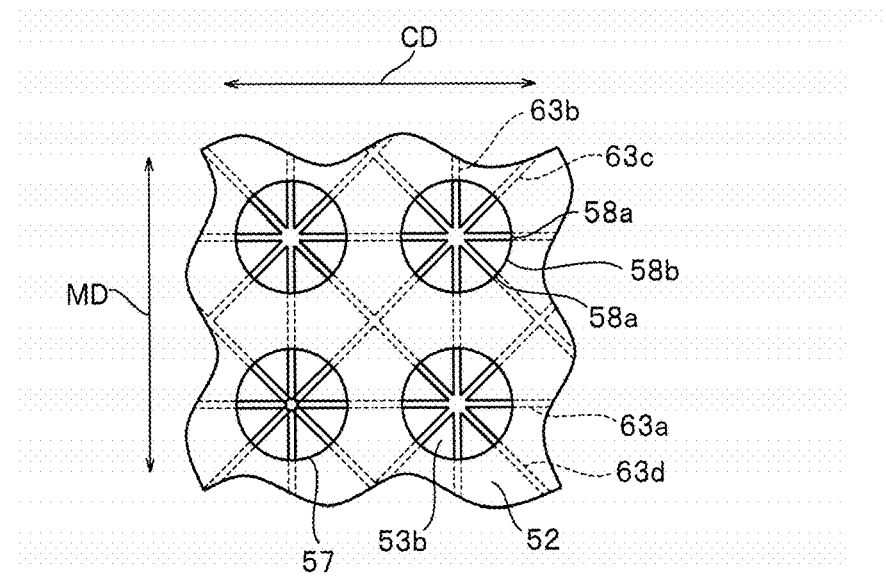
FIG. 31 is a main part schematic view illustrating a position relationship between penetration holes formed on an outer side cylindrical body and concave groove portions provided on an inner side cylindrical body.

In the above-mentioned Embodiment 2 (FIG. 23) and Embodiment 3 (FIG. 31), not only linear-shaped first concave groove portions 62*a*, 63*a* along the C direction but also a plurality of second concave groove portions 62*b*, 63*b* along the circumferential direction of the cylinder which is to be the M direction and the third and fourth concave groove portions 63*c*, 63*d* at an inclination angle of 45° in the C direction or the M direction are also concaved on the outer peripheral surface of the inner side cylindrical bodies 53*a*, 53*b* with respect to one circular penetration hole 57 of the outer side cylindrical body 52 one by one.

However, in the present invention, also in the above-mentioned Embodiment 2 (FIG. 23) and Embodiment 3 (FIG. 31) as well as in the modification example 2 (FIG. 35) and the modification example 3 (FIG. 36), the size of the penetration hole 57 formed on the outer cylindrical body 52 is set to be large or the forming pitch of the concave groove portions 62, 63*a*-63*d*, 64, 65 formed on the inner side cylindrical bodies 53*a*, 53*b*, 53*d*, 53*e* are set to be small, thereby the arbitral number of concave groove portion 62, 63*a*-63*d*, 64, 65 can be formed respectively with respect to one circular penetration hole 57 of the outer side cylindrical body 52. Further, a plurality of concave groove portions with the different groove width dimension or with the different forming pitch can be also provided. Also by the above means, the molded surface fastener having the engaging element in which a plurality of pawl portions are protruded regularly or irregularly on the outer peripheral edge part of the engaging head portion can be obtained.

Figure 37:
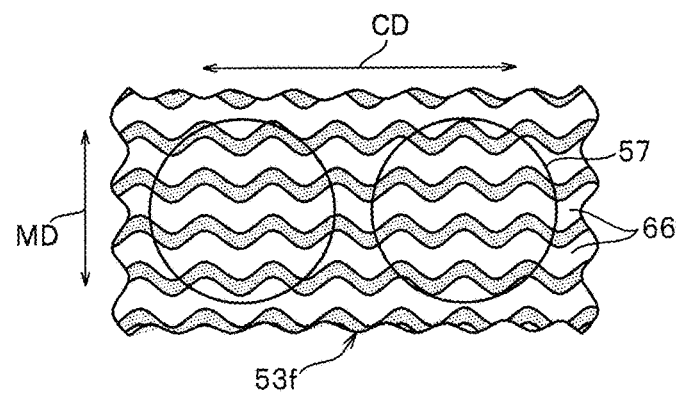
FIG. 37 is a main part schematic view illustrating a position relationship between penetration holes of an outer side cylindrical body and concave groove portions of an inner side cylindrical body according to modification example 4.

Next, in the modification example 4 as shown in FIG. 37, a plurality of concave groove portions 66 meandering as a wave along the C direction are concaved on the outer peripheral surface of the inner side cylindrical body 53*f* at a predetermined forming pitch. In the modification example 4, the size of the penetration hole 57 formed on the outer side cylindrical body 52 or the groove width dimension and the forming pitch of the concave groove portion 66 are changed, thereby one or a plurality of concave groove portions 66 can be formed with respect to one circular penetration hole 57 of the outer side cylindrical body 52.

Moreover, in the modification example 4, a plurality of concave groove portions 66 meandering as a wave are concaved on the outer peripheral surface of the inner side cylindrical body 53*f* along the C direction. However, in the present invention, a plurality of concave groove portions 66 meandering as a wave can be also concaved along the circumferential direction of the cylinder which is to be the M direction or along the direction inclining with a predetermined angle with respect to the C direction or the M direction.

Also by manufacturing the molded surface fastener using the inner side cylindrical body 53*f* on which a plurality of concave groove portions 66 meandering as a wave are concaved as in the modification example 4, the molded surface fastener having the engaging element in which a plurality of pawl portions are protruded regularly or irregularly on the outer peripheral edge part of the engaging head portion can be easily obtained.

Figure 38:
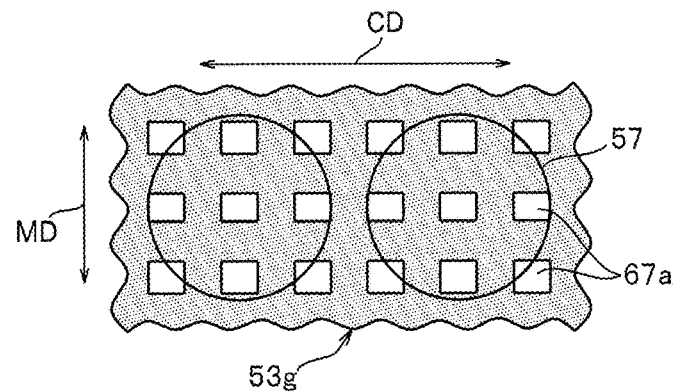
FIG. 38 is a main part schematic view illustrating a position relationship between penetration holes of an outer side cylindrical body and concave groove portions of an inner side cylindrical body according to modification example 5.

The modification example 5 shown in FIG. 38 is totally in contrast to the case of the inner side cylindrical body 53*a* of the above-mentioned Embodiment 2 in which the concave groove portion 62 is formed along the C direction and the M direction. A plurality of rectangular-shaped concave portion (recess) 67*a* are formed at a predetermined interval not only in the C direction but also in the M direction so as the outer peripheral surface of the cylinder of the inner side cylindrical body 53*g* to remain along the C direction and the M direction.

A plurality of rectangular-shaped concave portion 67*a* are concaved on the outer peripheral surface of the inner side cylindrical body 53*g* in the modification example 5 so as the outer peripheral surface of the inner side cylindrical body 53*g* to remain along the C direction and the M direction as a lattice shape. However, in the present invention, a plurality of rectangular-shaped concave portions 67*a* can be also concaved so as the lattice shape of the outer peripheral surface of the inner side cylindrical body 53*g* to be formed in the direction inclining with a predetermined angle with respect to the C direction and the M direction.

Also by manufacturing the molded surface fastener using the inner side cylindrical body 53*g* of the modification example 5, the molded surface fastener having the engaging element in which a plurality of pawl portions are protruded regularly or irregularly on the outer peripheral edge part of the engaging head portion can be easily obtained.

Figure 39:
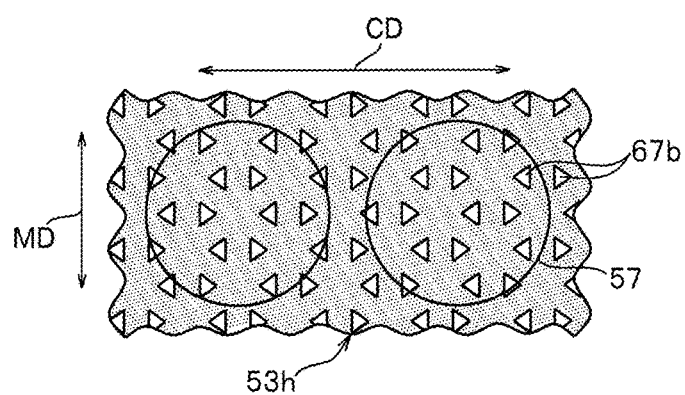
FIG. 39 is a main part schematic view illustrating a position relationship between penetration holes of an outer side cylindrical body and concave groove portions of an inner side cylindrical body according to modification example 6.

In the modification example 6 shown in FIG. 39, a plurality of triangle-shaped concave portions (recesses) 67*b* are concaved so as the outer peripheral surface of the cylinder of the inner side cylindrical body 53*h* to extend linearly in various directions (for example, to remain as a radial-shaped pattern). Also by the modification example 6, the size of the penetration hole 57 formed on the outer side cylindrical body 52 or the dimension and the forming pitch of the concave portion 67*b* can be appropriately changed. And also by manufacturing the molded surface fastener using the inner side cylindrical body 53*h* of the modification example 6, the molded surface fastener having the engaging element in which a plurality of pawl portions are protruded irregularly on the outer peripheral edge part of the engaging head portion can be easily obtained.

Figure 40:
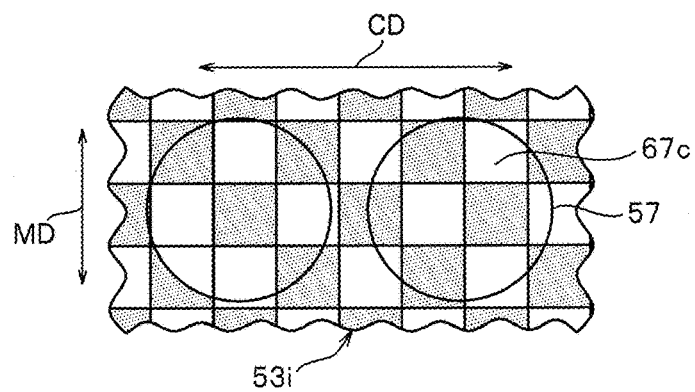
FIG. 40 is a main part schematic view illustrating a position relationship between penetration holes of an outer side cylindrical body and concave groove portions of an inner side cylindrical body according to modification example 7.

In the modification example 7 shown in FIG. 40, the outer peripheral surface of the cylinder of the inner side cylindrical body 53*i* and the square-shaped concave portions (recesses) 67*c* are concaved so as to form a checkered pattern. Also in the modification example 7, the size of the penetration hole 57 formed on the outer cylindrical body 52 or the dimension and the forming pitch of the concave portion 67*c* can be appropriately changed. Further, in the modification example 7, the checkered pattern formed by the concave portion 67*c* is formed along the circumferential direction of the cylinder which is to be the C direction and the M direction. However, in the present invention, the checkered pattern formed by the outer peripheral surface of the inner side cylindrical body 53*i* and the concave portion 67*c* can be formed along the direction inclining with a predetermined angle with respect to the C direction and the M direction. Also by manufacturing the molded surface fastener using the inner side cylindrical body 53*i* of the modification example 7, the molded surface fastener having the engaging element in which a plurality pawl portions are protruded regularly or irregularly on the outer peripheral edge part of the engaging head portion can be easily obtained.

Figure 41:
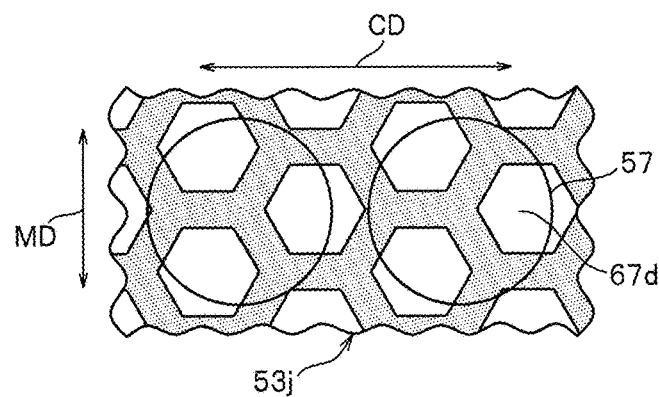
FIG. 41 is a main part schematic view illustrating a position relationship between penetration holes of an outer side cylindrical body and concave groove portions of an inner side cylindrical body according to modification example 8.

In the modification example 8 shown in FIG. 41, a plurality of regular hexagon-shaped concave portions (recesses) 67*d* are formed on the outer peripheral surface of the inner side cylindrical body 53*j* at a predetermined interval so as the outer peripheral surface of the inner side cylindrical body 53*j* to remain as a tortoiseshell-like pattern. Also in the modification example 7, the size of the penetration hole 57 formed on the outer side cylindrical body 52 or the size and the forming pitch of the regular hexagon-shaped concave portion 67*d* can be appropriately changed, and the regular hexagon-shaped concave portion 67*d* can be also formed so as to slope with respect to the C direction or the M direction. Also by manufacturing the molded surface fastener using the inner side cylindrical body 53*j* of the above modification example 8, the molded surface fastener having the engaging element in which a plurality of pawl portions are protruded regularly or irregularly on the outer peripheral edge part of the engaging head portion can be easily obtained.

Since a plurality of pawl portions are protruded regularly or irregularly on the engaging head portion of each engaging element in each molded surface fastener manufactured using the inner side cylindrical bodies 53*c*-53*j* shown in the above-mentioned modification example 1-the modification example 8, the molded surface fasteners have a strong engaging force with respect to the female surface fastener having loops stably and a texture of the surface (upper surface) of the molded surface fastener can be comfortable.

In the above-mentioned Embodiment 1-Embodiment 3 and the modification example 1-the modification example 8, the cases that the molded surface fastener is manufactured using the manufacturing apparatus 40 shown in FIG. 10 are explained. However, in the present invention, it is possible that the molded surface fasteners according to the above-mentioned Embodiment 1-Embodiment 3 and the modification example 1-the modification example 8 are manufactured by using a manufacturing apparatus 40*a* according to the first modification example shown in FIG. 42 or a manufacturing apparatus 40*b* according to the second modification example 2 shown in FIG. 43.

Figure 42:
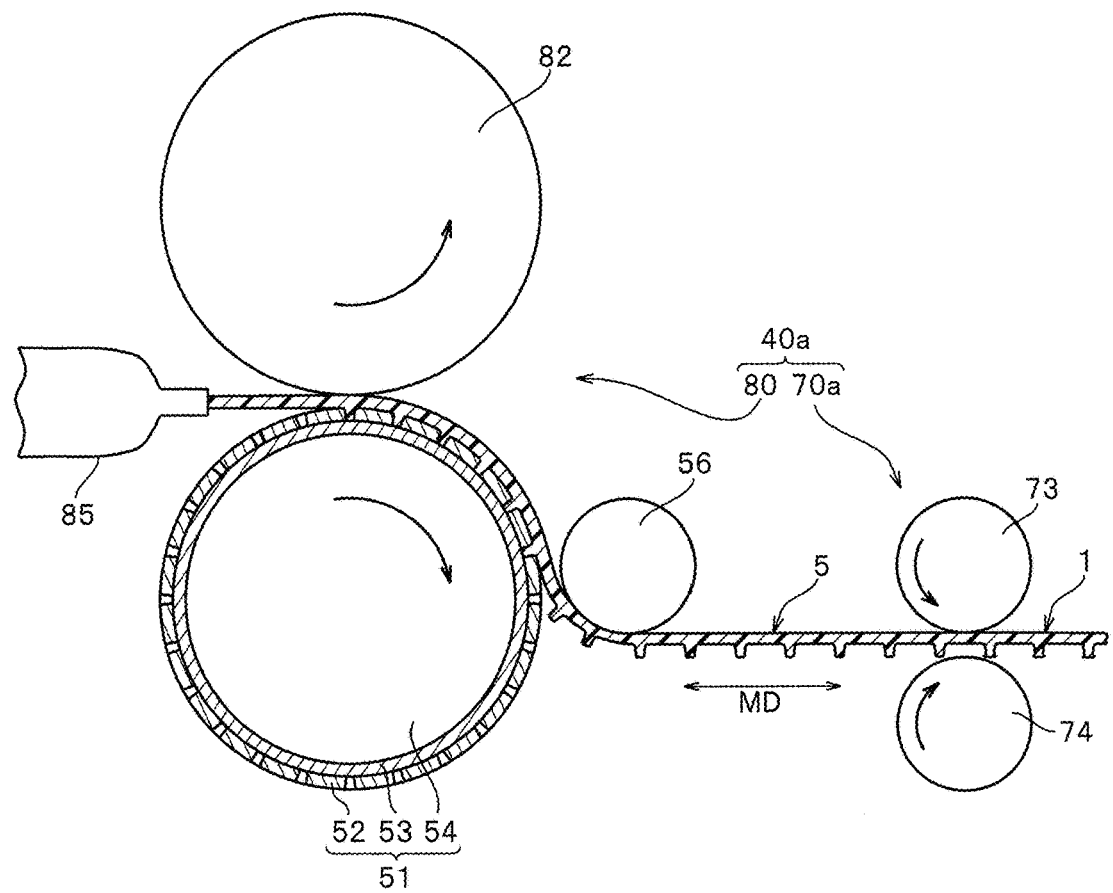
FIG. 42 is a schematic view illustrating a manufacturing apparatus of a molded surface fastener according to a first modification example schematically.

For example, the manufacturing apparatus 40*a* according to the first modification example shown in FIG. 42 has a molding apparatus 80 conducting the primary molding step and a heat press apparatus 70*a* heating and pressing the primary molded body 5 formed in the primary molding step.

The molding apparatus 80 according to the first modification example has a die wheel 51 rotating drivingly in one direction (in a clockwise direction in Figures), a press roller 82 disposed on an upper side of the die wheel 51 at a predetermined interval and rotating drivingly in an opposite direction to the die wheel 51 (in a counterclockwise direction in Figures), an extrusion nozzle 85 extruding the molten synthetic resin material continuously between the die wheel 51 and the press roller 82 and a pickup roller 56 disposed at a downstream side in the rotating direction of the die wheel 51 compared to the extrusion nozzle 85.

In this case, the die wheel 51 of the first modification example has substantially the same structure as the die wheel 51 of Embodiment 1 shown in FIG. 10. That is, a plurality of penetration holes 57 as shown in FIGS. 11-13 are drilled on the outer side cylindrical body 52 of the die wheel 51 corresponding to an arrangement of the engaging element 10 of the molded surface fastener 1 to be manufactured so as to penetrate from the outer peripheral surface to the inner peripheral surface of the outer side cylindrical body 52.

A plurality of concave groove portions 61 are concaved and linearly on the outer peripheral surface of the inner side cylindrical body 53 along the C direction orthogonal to the M direction in which the primary molded body 5 flows. Further, in this case, an interval between the die wheel 51 and the press roller 82 is adjusted so as to correspond to a thickness dimension of the base portion 2 of the molded surface fastener 1 to be manufactured.

The heat press apparatus 70*a* according to the first modification example has a pair of upper and lower pressing rollers 73, 74 disposed at a downstream side of the pickup roller 56, and the upper side pressing roller 73 and the lower side pressing roller 74 are disposed opposing at a predetermined interval. An interval between the upper side and the lower side pressing rollers 73, 74 can be adjusted by a height adjustment means not shown in Figures.

The lower side pressing roller 74 according to the first modification example has the same structure as the upper side pressing roller 71 in the heat press apparatus 70 of Embodiment 1 shown in FIG. 10, and is disposed so as to rotate in a counterclockwise direction in FIG. 42. Further, the upper side pressing roller 73 according to the first modification example has the same structure as the lower side pressing roller 72 in the heat press apparatus 70 of Embodiment 1 shown in FIG. 10, and forms a supporting surface supporting the primary molded body 5 to be conveyed.

In a case of manufacturing the molded surface fastener 1 using the manufacturing apparatus 40*a* of the first modification example shown in FIG. 42, firstly, the primary molding step for molding the primary molded body 5 by the molding apparatus 80 is conducted. In the primary molding step, the molten synthetic resin material is extruded continuously from the extrusion nozzle 85 between the die wheel 51 and the press roller 82, thereby the base portion 2 is formed by a space between the die wheel 51 and the press roller 82, and a plurality of provisional elements 20 are molded on the base portion 2 by the outside and inner side cylindrical bodies 52, 53 of the die wheel 51. Thus, the primary molded body 5 is manufactured.

The primary molded body 5 molded in the primary molding step is solidified by being held on the outer peripheral surface of the die wheel 51, cooled and half rotated, and thereafter, peeled off continuously from the outer peripheral surface of the die wheel 51 by the pickup roller 56. Thus, the primary molded body 5 having a plurality of provisional elements 20 on the base portion 2 can be obtained.

Then, the primary molded body 5 peeled off from the die wheel 51 is conveyed toward the heat press apparatus 70a conducting the secondary molding step in a state the upper side and the lower side are upside down, and introduced between the upper side pressing roller 73 and the lower side pressing roller 74 of the heat press apparatus 70a. Due to the above means, each provisional element 20 of the primary molded body 5 is heated and pressed by the lower side pressing roller 74 and the upper end part of each provisional element 20 can be compressed. Thus, the molded surface fastener 1 according to Embodiment 1 can be stably manufactured. In this case, the molded surface fasteners according to the above-mentioned Embodiment 2 and Embodiment 3, and the modification example 1-the modification example 8 can be also easily and stably manufactured by changing the forming pattern of the concave groove portion or the concave portion concaved on the outer peripheral surface of the inner side cylindrical body 53.

Figure 43:
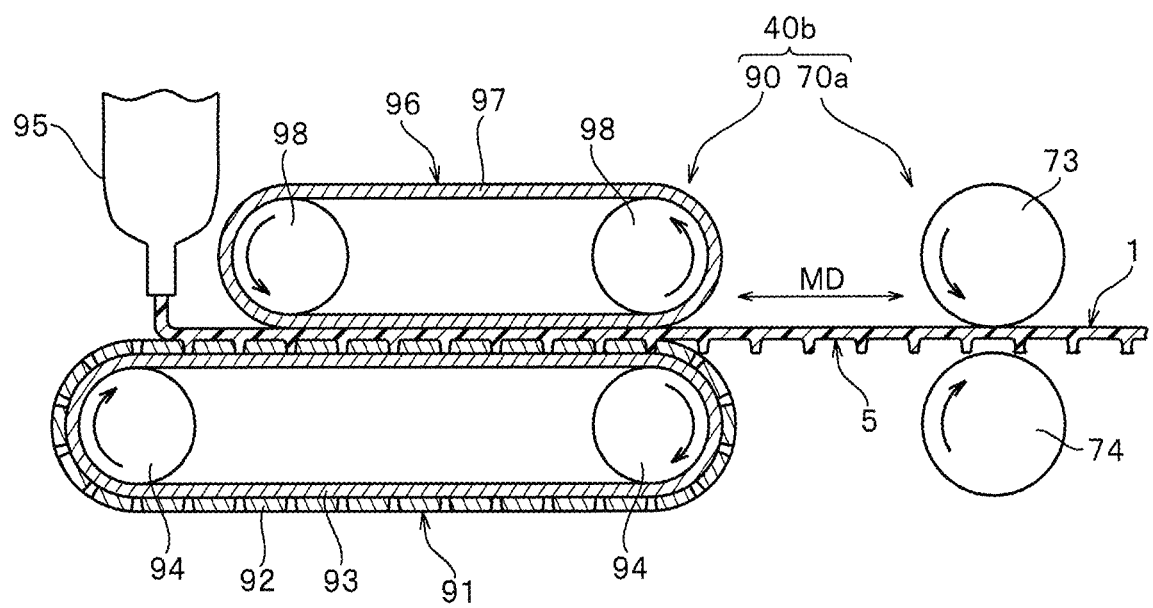
FIG. 43 is a schematic view illustrating a manufacturing apparatus of a molded surface fastener according to a second modification example schematically.
Figure 44:
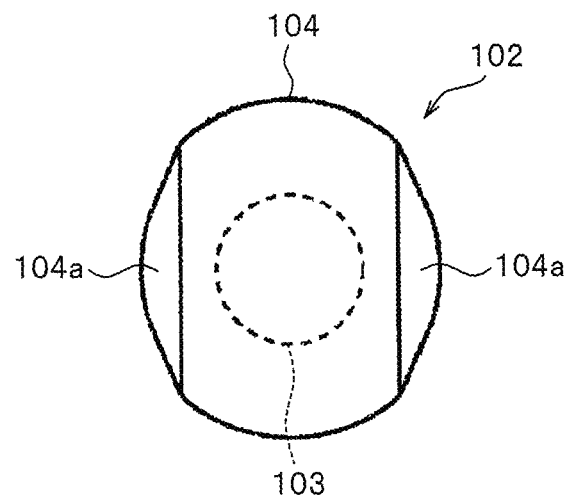
FIG. 44 is a plan view illustrating a conventional engaging element.
Figure 45:
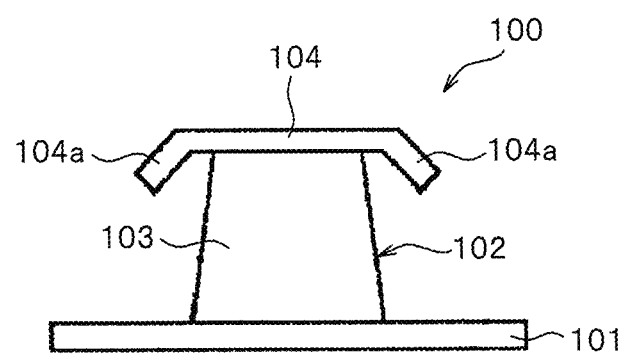
FIG. 45 is a side view illustrating a surface fastener having the engaging element.
Figure 46:
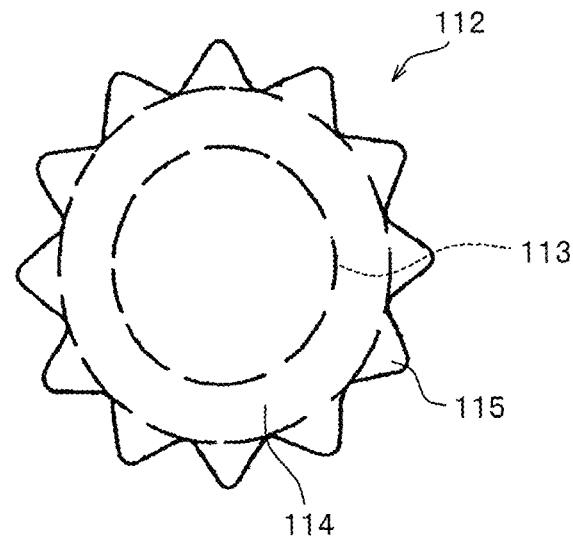
FIG. 46 is a plan view illustrating another conventional engaging element.
Figure 47:
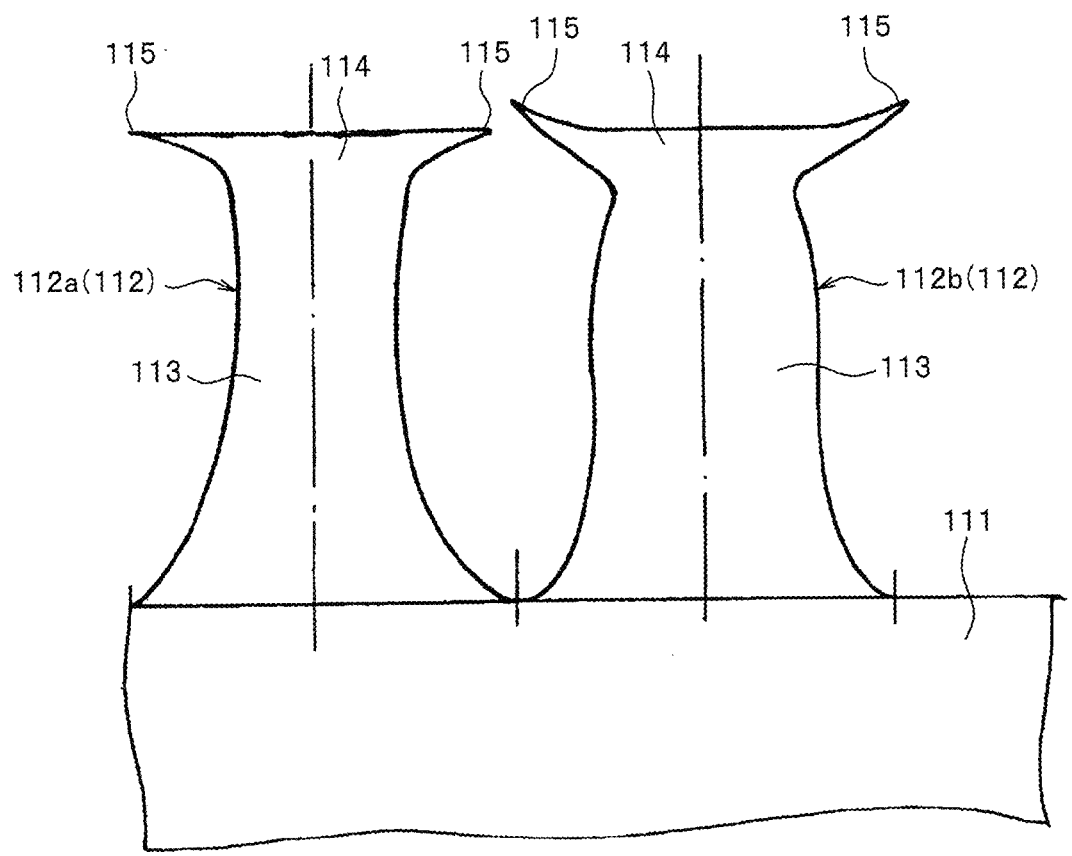
FIG. 47 is a side view illustrating a surface fastener having the engaging element.

Next, the manufacturing apparatus 40b according to the second modification example shown in FIG. 43 has a molding apparatus 90 conducting the primary molding step and a heat press apparatus 70a heating and pressing the primary molded body 5 molded in the primary molding step. In this case, the heat press apparatus 70a according to the second modification example is formed substantially the same as the heat press apparatus 70a according to the above-mentioned first modification example.

The molding apparatus 90 according to the second modification example has a molding side belt mechanism 91 running rotationally in one direction (in a clockwise direction in Figures), a press side belt mechanism 96 disposed on the upper side of the molding side belt mechanism 91 at a predetermined interval and running rotationally in an opposite direction to the molding side belt mechanism 91 (in a counterclockwise direction in Figures) and an extrusion nozzle 95 disposed opposing to the outer peripheral surface of the belt of the molding side belt mechanism 91 and extruding the molten synthetic resin material continuously.

The molding side belt mechanism 91 of the second modification example has an outer side endless belt 92 to be a mold, an inner side endless belt 93 disposed closely contacting with the inside of the outer side endless belt 92 and a pair of first rotating rollers 94 which the outside and the inner side endless belts 92, 93 are wound around and which make the outside and the inner side endless belts 92, 93 run rotationally, and can make the outside and the inner side endless belts 92, 93 rotate synchronically.

A plurality of penetration holes 57 which are the same as the penetration holes 57 provided on the outer side cylindrical body 52 (see FIGS. 11-13) of the above-mentioned Embodiment 1 are drilled on the outer side endless belt 92. Each penetration hole 57 is formed at a position of the outer side endless belt 92 corresponding to the arrangement of the engaging element 10 of the molded surface fastener to be manufactured penetrating from the outer peripheral surface to the inner peripheral surface of the outer side endless belt 92.

A plurality of concave groove portions are concaved on the outer peripheral surface of the inner side endless belt 93. Each concave groove portion is formed linearly along the C direction with a size with which the synthetic resin forming the molded surface fastener 1 in a molten state can flow into. In the second modification example, each concave groove portion formed on the inner side endless belt 93 has the same size and cross-sectional shape as in the case of the inner side cylindrical body 53 (see FIGS. 11-13) of the above-mentioned Embodiment 1, and are formed at a position of overlapping with a diameter of the penetration hole 57 formed on the outer side endless belt 92 in the M direction at a predetermined pitch.

Also in the second modification example, when viewing a position relationship between the penetration hole 57 provided on the outer side endless belt 92 and the concave groove portion provided on the inner side endless belt 93, the circular-shaped outer peripheral edge of each penetration hole 57 disposed on the inner peripheral surface of the outer side endless belt 92 has a groove overlapped part overlapping with the concave groove portion of the inner side endless belt 93 and an arc-shaped close contacting part directly contacting with the outer peripheral surface of the inner side endless belt 93.

The press side belt mechanism 96 has an endless belt for pressing 97 and a pair of second rotating rollers 98 which the endless belt for pressing 97 are wound around and which make the endless belt for pressing 97 run rotationally.

Further, in this case, an interval between the molding side belt mechanism 91 and the press side belt mechanism 96 (that is, an interval between an outer surface of the outer side endless belt 92 in the molding side belt mechanism 91 and an outer surface of the endless belt for pressing 97 of the press side belt mechanism 96) is adjusted to be a size corresponding to the thickness dimension of the base portion 2 of the molded surface fastener 1 to be manufactured.

In a case of manufacturing the molded surface fastener 1 using such a manufacturing apparatus 40b of the second modification example shown in FIG. 43, firstly, the primary molding step for molding the primary molded body 5 by the molding apparatus 90 is conducted. In the primary molding step, while driving rotationally the molding side belt mechanism 91 and the press side belt mechanism 96, the molten synthetic resin material is extruded continuously from an extrusion nozzle 95 to the outer surface of the outer side endless belt 92 of the molding side belt mechanism 91.

Thereby, the base portion 2 is molded between the outer side endless belt 92 of the molding side belt mechanism 91 and the endless belt for pressing 97 of the press side belt mechanism 96, and a plurality of provisional elements 20 are molded on the base portion 2 by the outside and the inner side endless belts 92, 93 of the molding side belt mechanism 91. Thus, the primary molded body 5 is manufactured.

The primary molded body 5 molded in the primary molding step is solidified by flowing along the machine direction between the molding side belt mechanism 91 and the press side belt mechanism 96. Particularly, in the molding apparatus 90 of the second modification example, compared to the above-mentioned Embodiment 1 (see FIG. 10) or the case of the first modification example (see FIG. 42), the primary molded body 5 can be conveyed linearly when cooling, and the speed of conveyance and the length of conveyance can be easily adjusted. Therefore, an advantage that the primary molded body 5 can be efficiently molded and the primary molded body 5 to be molded is hard to deform can be obtained.

Then, the cooled and solidified primary molded body 5 is peeled off from the molding side belt mechanism 91 such that it is pulled by a conveyance roller not shown in Figures from a space between the molding side belt mechanism 91 and the press side belt mechanism 96. Thereafter, the primary molded body 5 is conveyed toward the heat press apparatus 70a in a state that the upper direction and the lower direction are upside down, and introduced between the upper side pressing roller 73 and the lower side pressing roller 74 of the heat press apparatus 70a.

Due to the above means, each provisional element 20 of the primary molded body 5 are heated and pressed by the lower side pressing roller 74, and the upper end part of each provisional element 20 can be compressed. Therefore, the molded surface fastener 1 according to Embodiment 1 can be stably manufactured. Further, in this case, the molded surface fasteners according to the above-mentioned Embodiment 2 and Embodiment 3, and the modification example 1—the modification example 8 can be easily and stably manufactured by changing the forming pattern of the concave groove portion or the concave portion concaved on the outer peripheral surface of the inner side endless belt 93.

REFERENCE SIGNS LIST 1, 1a, 1b Molded surface fastener
2 Base portion
5, 5a, 5b Primary molded body
10 Engaging element
10a, 10b Engaging element
11 Stem portion
12 Engaging head portion
13a Top end surface of head portion
13b Back surface of head portion
13c Outer peripheral side surface
14 Pawl portion
15a Upper surface of pawl
15b Back surface of pawl (Lower surface)
15c Side wall surface
16 Boundary
20 Provisional element
20a, 20b Provisional element
21 Primary stem portion
22 Bulging portion
22a, 22b Bulging portion
25 Protruded portion (Provisional pawl portion)
40 Manufacturing apparatus
40a, 40b Manufacturing apparatus
50 Molding apparatus
51 Die wheel
52 Outer side cylindrical body (Outer side sleeve)
53 Inner side cylindrical body (Inner side sleeve)
53a-53j Inner side cylindrical body (Inner side sleeve)
54 rotational driving roller
55 Extrusion nozzle
56 Pickup roller
57 Penetration hole
58a Groove overlapped part
58b Close contacting part
61 Concave groove portion
62 Concave groove portion
62a First concave groove portion
62b Second concave groove portion
63a First concave groove portion
63b Second concave groove portion
63c Third concave groove portion
63d Fourth concave groove portion
64, 65, 66 Concave groove portion
67a, 67b Concave portion (Recess)
67c, 67d Concave portion (Recess)
70, 70a Heat press apparatus
71 Upper side pressing roller (Calender roller)
72 Lower side pressing roller (Calender roller)
73 Upper side pressing roller
74 Lower side pressing roller
80 Molding apparatus
82 Press roller
85 Extrusion nozzle
90 Molding apparatus
91 Molding side belt mechanism
92 Outer side endless belt
93 Inner side endless belt
94 First rotating roller
95 Extrusion nozzle
96 Press side belt mechanism
97 Endless belt for pressing
98 Second rotating roller
A Height dimension of engaging element
B Diameter of engaging head portion
C Height dimension of engaging head portion
D Diameter of engaging element at boundary
E Bulging dimension of engaging head portion
F Pawl width dimension
G Pawl length dimension
θ1 Bulging angle of engaging head portion
θ2 Pawl protruding angle
MD Machine direction
CD Crossing direction

The invention claimed is:

1. A molding apparatus used for manufacturing a molded surface fastener comprising a die wheel driving rotationally in one direction and an extrusion nozzle extruding a molten synthetic resin material toward the die wheel, wherein:

the die wheel has an outer side cylindrical body and an inner side core disposed in contact with an inner peripheral surface of the outer side cylindrical body, a plurality of penetration holes penetrating from an outer peripheral surface to an inner peripheral surface on the outer side cylindrical body, and concavo-convex patterns are formed on an outer peripheral surface of the inner side core, wherein the concavo-convex patterns communicate with at least one penetration hole of the outer side cylindrical body, wherein each of the penetration holes has an outer peripheral edge disposed on the inner peripheral surface of the outer side cylindrical body, the outer peripheral edge of the at least one penetration hole has at least one resin inflow part in which the outer peripheral edge overlaps with a concave portion in a part of the concavo-convex patterns to form a gap through which the molten synthetic resin material can flow between the outer peripheral edge and the outer peripheral surface of the inner side core and at least one contacting part in which the outer peripheral edge overlaps with a convex portion in a part of the concavo-convex patterns to regulate flowing of the molten synthetic resin material, the convex portion extends from the at least one contacting part of the outer peripheral edge to an inside of the at least one penetration hole, the concave portion is disposed between two of the convex portions on the outer peripheral edge, and the concave portion of the concavo-convex patterns has a size allowing the molten synthetic resin material to flow in the concave portion from the penetration hole to form a protruded portion.

2. The molding apparatus according to claim 1, wherein the concavo-convex patterns include a plurality of concave portions and a plurality of convex portions.

3. The molding apparatus according to claim 1, wherein the concavo-convex patterns include at least one continuous concave portion communicating with at least two penetration holes.

\* \* \* \* \*